(12) United States Patent
Ogawa et al.

(10) Patent No.: US 10,529,932 B2
(45) Date of Patent: *Jan. 7, 2020

(54) ORGANIC-ELECTROLUMINESCENT-ELEMENT MATERIAL AND ORGANIC ELECTROLUMINESCENT ELEMENT USING SAME

(71) Applicant: NIPPON STEEL & SUMIKIN CHEMICAL CO., LTD., Tokyo (JP)

(72) Inventors: Junya Ogawa, Kitakyushu (JP); Takahiro Kai, Kitakyushu (JP); Tokiko Ueda, Kitakyushu (JP); Masashi Tada, Kitakyushu (JP); Masaki Komori, Kitakyushu (JP); Toshihiro Yamamoto, Tokyo (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/117,440

(22) PCT Filed: Feb. 26, 2015

(86) PCT No.: PCT/JP2015/055579
§ 371 (c)(1),
(2) Date: Aug. 8, 2016

(87) PCT Pub. No.: WO2015/146455
PCT Pub. Date: Oct. 1, 2015

(65) Prior Publication Data
US 2016/0351827 A1 Dec. 1, 2016

(30) Foreign Application Priority Data
Mar. 24, 2014 (JP) .................................. 2014-059924

(51) Int. Cl.
*C07F 5/02* (2006.01)
*H01L 51/00* (2006.01)
(Continued)

(52) U.S. Cl.
CPC ........ *H01L 51/0072* (2013.01); *C07D 519/00* (2013.01); *C09K 11/025* (2013.01);
(Continued)

(58) Field of Classification Search
CPC ..................................................... C07F 5/027
See application file for complete search history.

(56) References Cited

U.S. PATENT DOCUMENTS

2008/0085463 A1 4/2008 Dammel et al.
2009/0167162 A1 7/2009 Lin et al.
(Continued)

FOREIGN PATENT DOCUMENTS

CN 103509043 A 1/2014
JP 2005-162709 A 6/2005
(Continued)

OTHER PUBLICATIONS

Thomas Hofbeck and Hartmut Yersin, the triplet state of fac-Ir(ppy)3, Inorganic Chemistry Sep. 20, 2010 49 (20), 9290-9299. (Year: 2010).*

(Continued)

*Primary Examiner* — Jennifer A Chriss
*Assistant Examiner* — Sean M DeGuire
(74) *Attorney, Agent, or Firm* — Cheng Law Group, PLLC

(57) ABSTRACT

Disclosed are an organic electroluminescent device that is improved in luminous efficiency, sufficiently secures driving stability, and has a simple construction, and a material to be used in the device. The material is a material for an organic electroluminescent device formed of a carborane ring com- (Continued)

pound having a structure in which two indolocarbazole groups are each bonded to a carborane ring through an aromatic group. In addition, the device is an organic electroluminescent device having organic layers between an anode and a cathode laminated on a substrate, in which at least one layer of the organic layers contains the material for an organic electroluminescent device. When the organic layer is a light-emitting layer, the layer contains a phosphorescent light-emitting dopant and contains the material for an organic electroluminescent device as a host material.

2 Claims, 1 Drawing Sheet

(51) Int. Cl.
*C07D 519/00* (2006.01)
*C09K 11/06* (2006.01)
*C09K 11/02* (2006.01)
*H01L 51/50* (2006.01)
*H01L 51/56* (2006.01)

(52) U.S. Cl.
CPC .......... *C09K 11/06* (2013.01); *H01L 51/0045* (2013.01); *H01L 51/0085* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *C09K 2211/188* (2013.01); *H01L 51/0081* (2013.01); *H01L 51/5016* (2013.01); *H01L 51/5056* (2013.01); *H01L 51/5072* (2013.01); *H01L 51/56* (2013.01)

(56) References Cited

U.S. PATENT DOCUMENTS

| 2010/0176386 A1 | 7/2010 | Yersin et al. |
| 2011/0278556 A1* | 11/2011 | Kottas ..................... C07F 5/027 257/40 |
| 2014/0332792 A1 | 11/2014 | Tada et al. |
| 2016/0380199 A1* | 12/2016 | Ogawa ................ C09K 11/025 257/40 |

FOREIGN PATENT DOCUMENTS

| JP | 2005-166574 A | | 6/2005 |
| JP | 2005166574 A | * | 6/2005 |
| JP | 2010-59128 A | | 3/2010 |
| WO | WO-2013/094834 A1 | | 6/2013 |

OTHER PUBLICATIONS

International Search Report for the Application No. PCT/JP2015/055579 dated May 19, 2015.
English Translation of the Written Opinion of the International Searching Authority (PCT/ISA/237) for Application No. PCT/JP2015/055579 dated Oct. 6, 2016.
Wee, Kyung-Ryang et al., "Carborane-Based Optoelectronically Active Organic Molecules: Wide Band Gap Host Materials for Blue Phosphorescence", Journal of the American Chemistry Society, 2012, vol. 134, pp. 17982-17990.
Supplementary European Search Report for the Application No. EP 15 76 9967 dated Oct. 5, 2017.

* cited by examiner

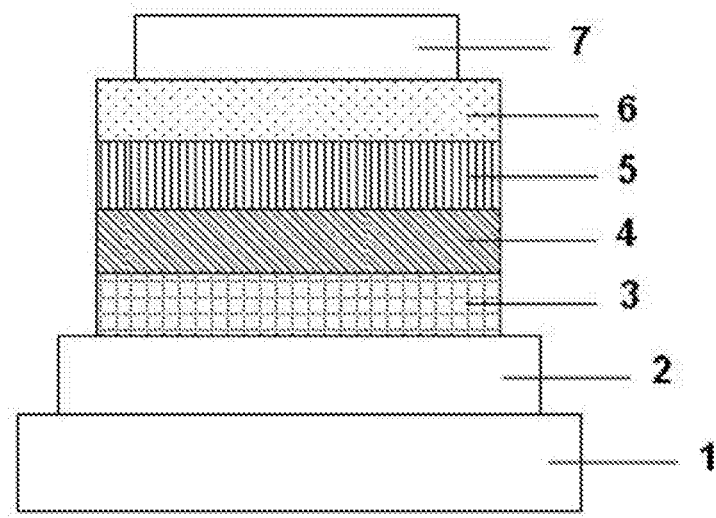

ORGANIC-ELECTROLUMINESCENT-ELEMENT MATERIAL AND ORGANIC ELECTROLUMINESCENT ELEMENT USING SAME

TECHNICAL FIELD

The present invention relates to an organic electroluminescent device using a carborane compound as a material for an organic electroluminescent device, and more specifically, to a thin film-type device that emits light by applying an electric field to a light-emitting layer containing an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex ($Alq_3$) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, investigations have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of $Alq_3$ are formed emit light by using fluorescent light emission. However, by using phosphorescent light emission, that is, by using light emission from a triplet excited state, luminous efficiency is expected to be improved by from about three times to about four times, as compared to the case of using related-art devices in which fluorescent light (singlet) is used. In order to accomplish this purpose, investigations have been made on adopting a coumarin derivative or a benzophenone derivative as a light-emitting layer, but extremely low luminance has only been provided. Further, investigations have been made on using a europium complex as an attempt to use a triplet state, but highly efficient light emission has not been accomplished. In recent years, many investigations have been made mainly on an organic metal complex, such as an iridium complex, for the purpose of attaining high luminous efficiency and a long lifetime.

CITATION LIST

Patent Literature

[PTL 1] WO 01/041512 A1
[PTL 2] JP 2001-313178 A
[PTL 3] JP 2005-162709 A
[PTL 4] JP 2005-166574 A
[PTL 5] WO 2013/094834 A1
[PTL 6] US 2009/0167162 A1

Non Patent Literature

[NPL 1] J. Am. Chem. Soc. 2012, 134, 17982-17990

In order to obtain high luminous efficiency, host materials that are used with the dopant materials described above play an important role. A typical example of the host materials proposed is 4,4'-bis(9-carbazolyl)biphenyl (CBP) as a carbazole compound disclosed in Patent Literature 2. When CBP is used as a host material for a green phosphorescent light-emitting material typified by a tris (2-phenylpyridine) iridium complex ($Ir(ppy)_3$), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from $Ir(ppy)_3$ lowers.

In order to provide high luminous efficiency to an organic EL device as described above, it is necessary to use a host material that has high triplet excitation energy, and is striking a good balance in both charge (hole and electron)-injecting/transporting property. Further desired is a compound that is electrochemically stable and has high heat resistance and excellent amorphous stability, and hence further improvement has been demanded.

In Patent Literatures 3, 4, 5, and 6 and Non Patent Literature 1, there are disclosures of such carborane compounds as shown below.

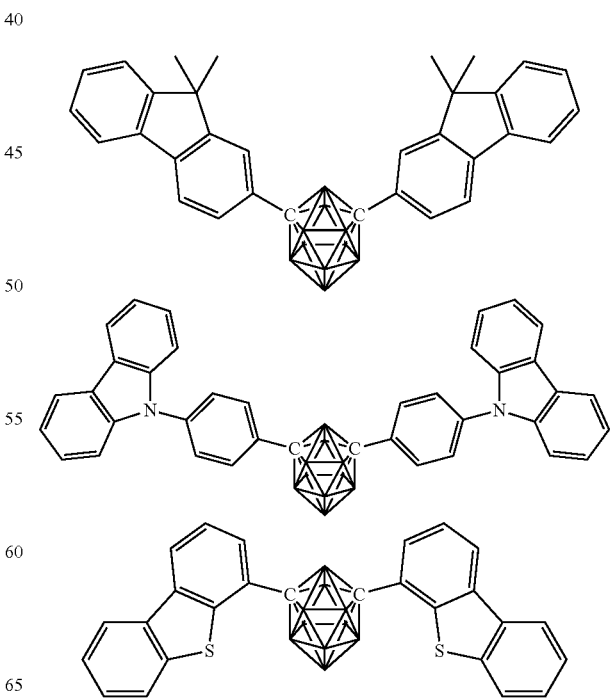

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high efficiency and high driving stability and is practically useful and a compound suitable for the organic EL device.

The inventors of the present invention have made extensive investigations, and as a result, have found that when a compound having at least one carborane group bonded onto an indolocarbazole group and having two indolocarbazole groups in a molecule thereof is used in an organic EL device, the device shows excellent characteristics. Thus, the inventors have completed the present invention.

The present invention relates to a material for an organic electroluminescent device including a carborane compound represented by the general formula (1).

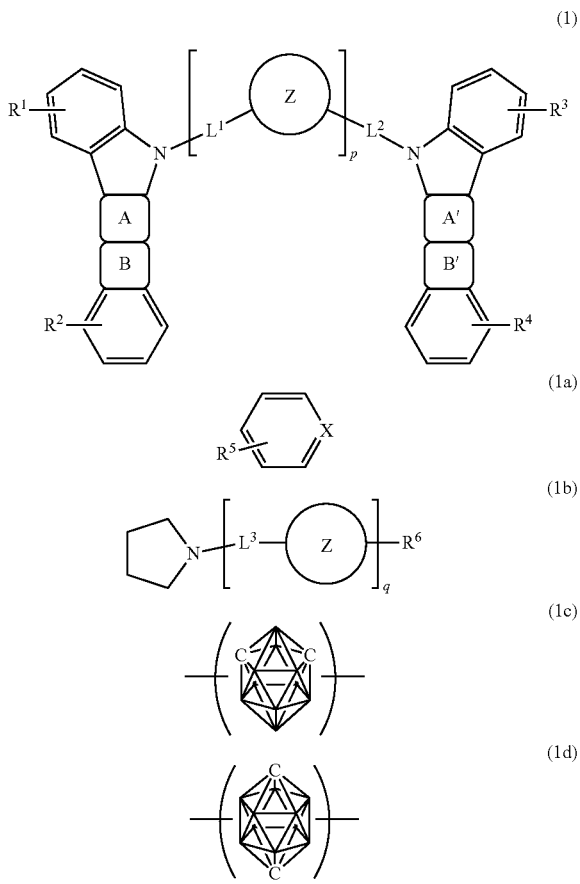

In the formula, a ring A and a ring A' each represent an aromatic ring represented by the formula (1a), the ring being fused with an adjacent ring at an arbitrary position, a ring B and a ring B' each represent a heterocycle represented by the formula (1b) whose nitrogen-containing five-membered ring is fused with an adjacent ring at an arbitrary position, X represents a methine group or a nitrogen atom, a ring Z represents a divalent carborane group $C_2B_{10}H_{10}$ represented by the formula (1c) or the formula (1d), and when the plurality of rings Z's are present in a molecule, the rings may be identical to or different from each other.

p and q each represent a number of repetitions, and each represent an integer of from 0 to 5, and at least one of p or two q's represents an integer of 1 or more, and the two formulae (1a) or the two formulae (1b) present in the same molecule may be identical to or different from each other.

$L^1$, $L^2$, and $L^3$ each independently represent a substituted or unsubstituted aromatic hydrocarbon group having 6 to 22 carbon atoms, a substituted or unsubstituted aromatic heterocyclic group having 3 to 18 carbon atoms, or a linked aromatic group formed by linking 2 to 6 arbitrary aromatic groups each selected from the substituted or unsubstituted aromatic hydrocarbon group and the substituted or unsubstituted aromatic heterocyclic group, and the linked aromatic group may be linear or branched.

$R^2$, $R^3$, $R^4$, $R^5$, and RE each independently represent a hydrogen atom, a substituted or unsubstituted aromatic hydrocarbon group having 6 to 22 carbon atoms, a substituted or unsubstituted aromatic heterocyclic group having 3 to 18 carbon atoms, or a linked aromatic group formed by linking 2 to 6 arbitrary aromatic groups each selected from the substituted or unsubstituted aromatic hydrocarbon group and the substituted or unsubstituted aromatic heterocyclic group, and the linked aromatic group may be linear or branched.

It is preferred that X in the general formula (1) represent a methine group, or the ring Z in the general formula (1) represent a divalent carborane group $C_2B_{10}H_8$ represented by the formula (1c).

It is preferred that, in the general formula (1), $L^1$, $L^2$, and $L^3$ each independently represent a substituted or unsubstituted aromatic hydrocarbon group having 6 to 18 carbon atoms, a substituted or unsubstituted aromatic heterocyclic group having 3 to 18 carbon atoms, or a linked aromatic group formed by linking 2 to 6 aromatic groups each selected from the aromatic hydrocarbon group and the aromatic heterocyclic group. It is more preferred that $L^1$, $L^2$, and $L^3$ each independently represent a substituted or unsubstituted aromatic heterocyclic group having 3 to 18 carbon atoms, or a linked aromatic group formed by linking 2 to 6 aromatic groups each selected from the aromatic heterocyclic group. Further, it is preferred that $R^1$ to $R^5$ each represent a hydrogen atom.

The present invention also relates to an organic electroluminescent device having a structure in which an anode, an organic layer, and a cathode are laminated on a substrate, in which the organic layer includes an organic layer containing the above-mentioned material for an organic electroluminescent device.

Further, it is preferred that the organic layer containing the material for an organic electroluminescent device include a phosphorescent light-emitting dopant. In addition, it is desired that the emission wavelength of the phosphorescent light-emitting dopant have an emission maximum wavelength at 600 nm or less.

The material for an organic electroluminescent device of the present invention adopts a structure having two indolocarbazole rings and at least one carborane group. In the carborane compound having such structural feature, the lowest unoccupied molecular orbital (LUMO) that affects an electron-injecting/transporting property is distributed on a carborane group, and the highest occupied molecular orbital (HOMO) that affects a hole-injecting/transporting property is distributed on each of the indolocarbazole rings. Accordingly, the charge-injecting/transporting properties of the device can be controlled at high levels by changing the number of carborane groups, or the kinds or number of substituents bonded to a carborane group or an indolocarbazole ring. Further, the compound enables efficient light emission from a dopant because the compound has the lowest triplet excitation energy (T1 energy) high enough to confine the T1 energy of the dopant. By virtue of the foregoing features, the use of the compound in an organic EL device can achieve a reduction in driving voltage of the device and high luminous efficiency.

In addition, the material for an organic electroluminescent device of the present invention shows a satisfactory amorphous characteristic and high heat stability, and at the same time, is extremely stable in an excited state. Accordingly, an organic EL device using the material has a long driving lifetime and durability at a practical level.

BRIEF DESCRIPTION OF DRAWINGS

The FIGURE is a sectional view for illustrating an example of the structure of an organic EL device.

DESCRIPTION OF EMBODIMENTS

A material for an organic electroluminescent device of the present invention is a carborane compound represented by the general formula (1). The carborane compound has at least one carborane group bonded thereto and has two indolocarbazole groups, and hence may exhibit an excellent effect.

In the general formula (1), $L^1$, $L^2$, and $L^3$ each independently represent a substituted or unsubstituted aromatic hydrocarbon group having 6 to 22 carbon atoms, a substituted or unsubstituted aromatic heterocyclic group having 3 to 18 carbon atoms, or a linked aromatic group. The term "linked aromatic group" as used herein refers to an aromatic group formed by linking 2 to 6 aromatic rings of an aromatic group selected from the unsubstituted aromatic hydrocarbon group having 6 to 22 carbon atoms, and the substituted or unsubstituted aromatic heterocyclic group having 3 to 18 carbon atoms in a chain manner. The linked aromatic group may be linear or branched, and the aromatic rings to be linked may be identical to or different from each other.

In the general formula (1), $R^1$ to $R^6$ each independently represent a hydrogen atom, a substituted or unsubstituted aromatic hydrocarbon group having 6 to 22 carbon atoms, a substituted or unsubstituted aromatic heterocyclic group having 3 to 18 carbon atoms, or a linked aromatic group. The term "linked aromatic group" as used herein refers to an aromatic group formed by linking 2 to 6 aromatic rings of an aromatic group selected from the unsubstituted aromatic hydrocarbon group having 6 to 22 carbon atoms, and the substituted or unsubstituted aromatic heterocyclic group having 3 to 18 carbon atoms in a chain manner. The linked aromatic group may be linear or branched, and the aromatic rings to be linked may be identical to or different from each other.

In the general formula (1), with regard to a group that may be present in plurality in a molecule, the groups may change independently of each other, even though the groups are represented by the same symbol. For example, with regard to each of $L^1$, $L^3$, the ring Z, the formula (1a), and the formula (1b), and X, $R^5$, $R^6$, and q present in the formulae (1a) and (1b), the same symbol may be present in plurality in a molecule, but those represented by the same symbol may be identical to or different from each other.

Specific examples of the unsubstituted aromatic hydrocarbon group include groups each produced by removing a hydrogen atom from an aromatic hydrocarbon compound, such as benzene, naphthalene, fluorene, anthracene, phenanthrene, triphenylene, tetraphenylene, fluoranthene, pyrene, or chrysene, or an aromatic hydrocarbon compound in which a plurality of those compounds are linked to each other. Of those, a group produced by removing a hydrogen atom from benzene, naphthalene, fluorene, phenanthrene, or triphenylene is preferred.

Specific examples of the unsubstituted aromatic heterocyclic group include linking groups each produced by removing a hydrogen atom from an aromatic heterocyclic compound, such as pyridine, pyrimidine, triazine, quinoline, isoquinoline, quinoxaline, quinazoline, naphthyridine, carbazole, acridine, azepine, tribenzazepine, phenazine, phenoxazine, phenothiazine, dibenzophosphole, or dibenzoborole, or an aromatic heterocyclic compound in which a plurality of those compounds are linked to each other. Of those, a group produced by removing a hydrogen atom from pyridine, pyrimidine, triazine, or carbazole is preferred.

The linked aromatic group produced by removing a hydrogen atom from an aromatic compound in which a plurality of aromatic hydrocarbon compounds or aromatic heterocyclic compounds are linked to each other is a group formed by linking 2 to 6 aromatic rings. The aromatic rings to be linked may be identical to or different from each other, and both an aromatic hydrocarbon group and an aromatic heterocyclic group may be included. The number of the aromatic rings to be linked is preferably from 2 to 4, more preferably 2 or 3.

Specific examples of the linked aromatic group include groups each produced by removing a hydrogen atom from biphenyl, terphenyl, phenylnaphthalene, diphenylnaphthalene, phenylanthracene, diphenylanthracene, diphenylfluorene, bipyridine, bipyrimidine, bitriazine, biscarbazole, phenylpyridine, phenylpyrimidine, phenyltriazine, phenylcarbazole, diphenylpyridine, diphenyltriazine, bis (carbazolyl)benzene, or the like.

The aromatic hydrocarbon group, the aromatic heterocyclic group, or the linked aromatic group may have a substituent. When any such group has a substituent, the substituent is preferably an alkyl group having 1 to 12 carbon atoms, an alkoxy group having 1 to 12 carbon atoms, or an acetyl group. The substituent is more preferably an alkyl group having 1 to 4 carbon atoms, an alkoxy group having 1 or 2 carbon atoms, or an acetyl group.

Here, when the linked aromatic group is a divalent group, the group is represented by, for example, any one of the following formulae, and its aromatic rings may be linked in a linear manner or a branched manner.

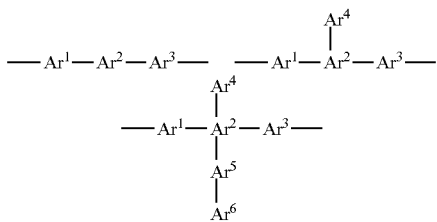

($Ar^1$ to $Ar^6$ each represent an unsubstituted aromatic hydrocarbon ring or aromatic heterocycle.)

In the general formula (1), p and q each represent a number of repetitions, and each represent an integer of from 0 to 5. Although one p and two q's may be present in the formula, at least one thereof represents an integer of 1 or more. The total of all p and q's is preferably from 1 to 3. The total of all p and q's is equal to the number of the rings Z in a molecule.

The ring A and the ring A' each represent an aromatic ring represented by the formula (1a), the ring being fused with an adjacent ring at an arbitrary position, and the ring B and the ring B' each represent a heterocycle represented by the formula (1b), the ring being fused with an adjacent ring at an arbitrary position, and a five-membered ring containing nitrogen is fused with the adjacent ring.

In the formula (1a), X represents a methine group or a nitrogen atom, preferably a methine group.

The ring Z represents a divalent carborane group ($C_2B_{10}H_{10}$) represented by the formula (1c) or (1d). The two bonding hands of the formula (1c) or (1d), which may each occur from C or from B, each preferably occur from C.

Of the carborane groups each represented by the formula (1c) or (1d), a carborane group represented by the formula (1c) is preferred.

The carborane compound represented by the general formula (1) can be synthesized from raw materials selected in accordance with the structure of the target compound by using a known approach.

(A-1) can be synthesized through the following reaction formula with reference to a synthesis example described in Journal of Organometallic Chemistry, 1993, 462, p19-29.

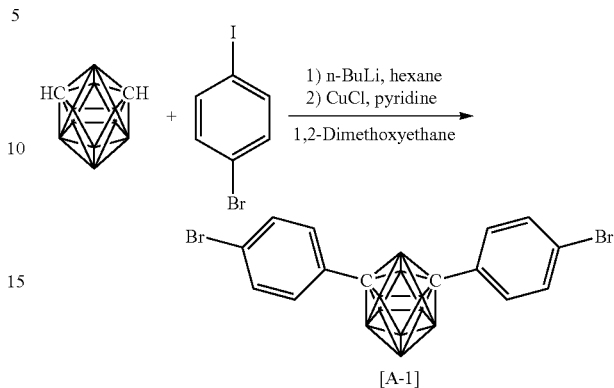

Specific examples of the carborane compound represented by the general formula (1) are shown below. However, the material for an organic electroluminescent device of the present invention is not limited thereto.

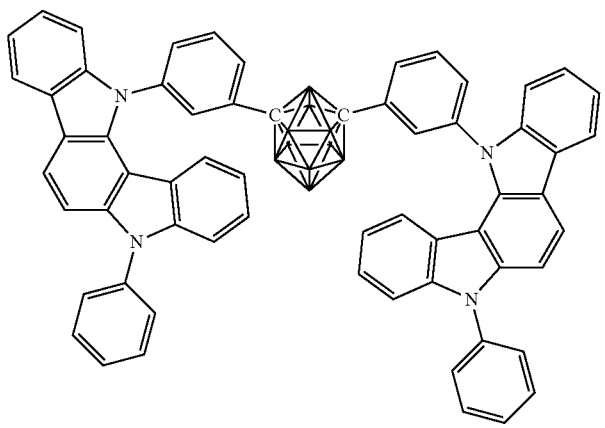

1

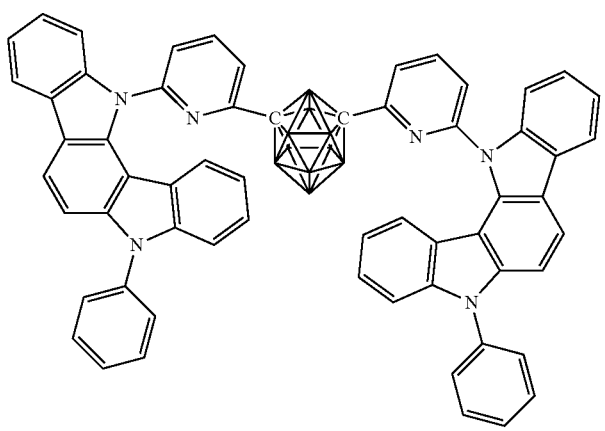

2

-continued
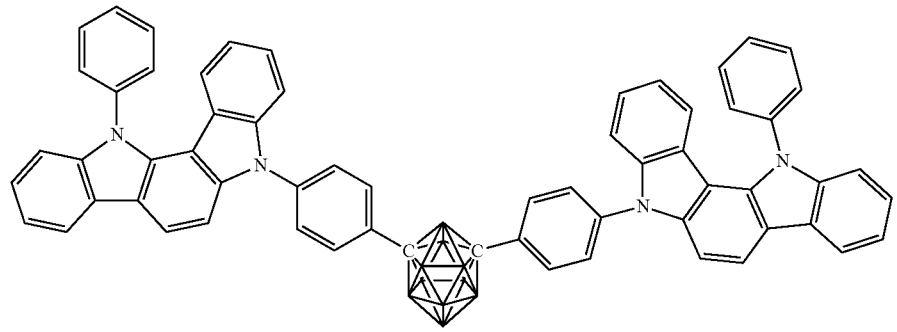
3
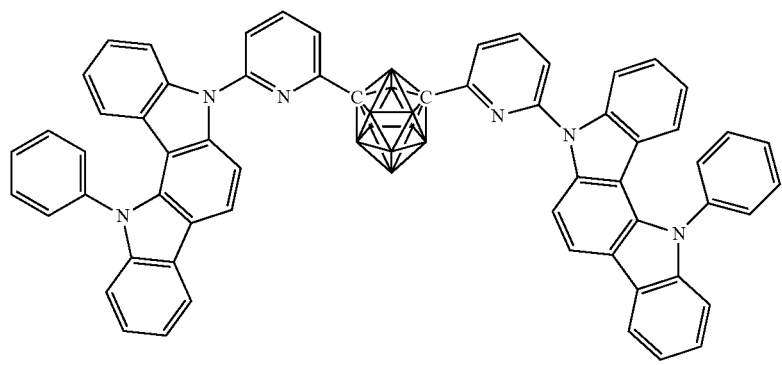
4
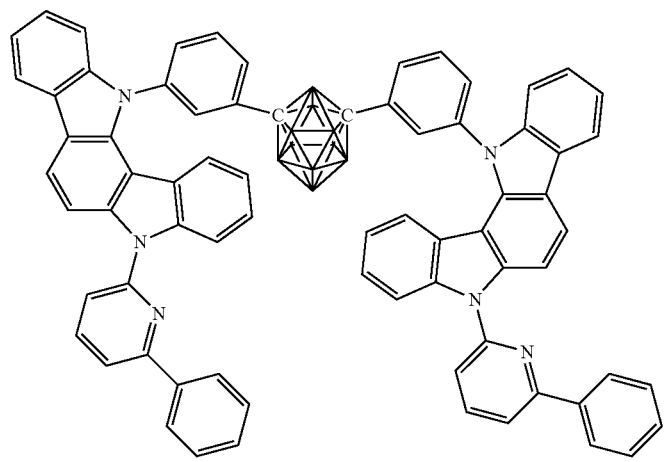
5
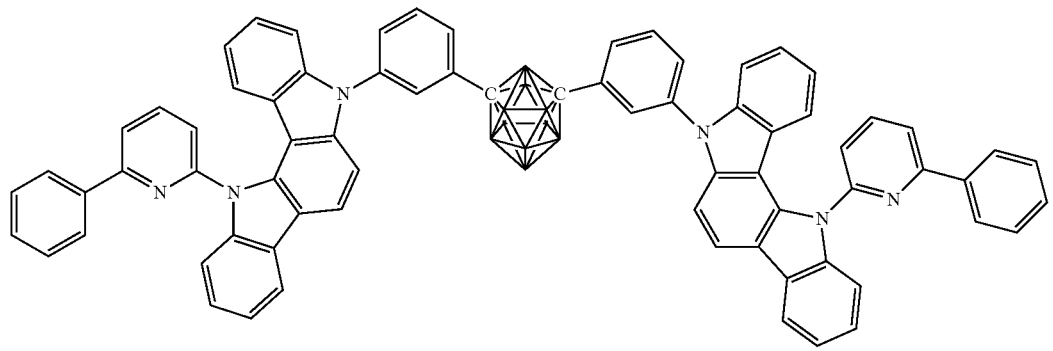
6

7
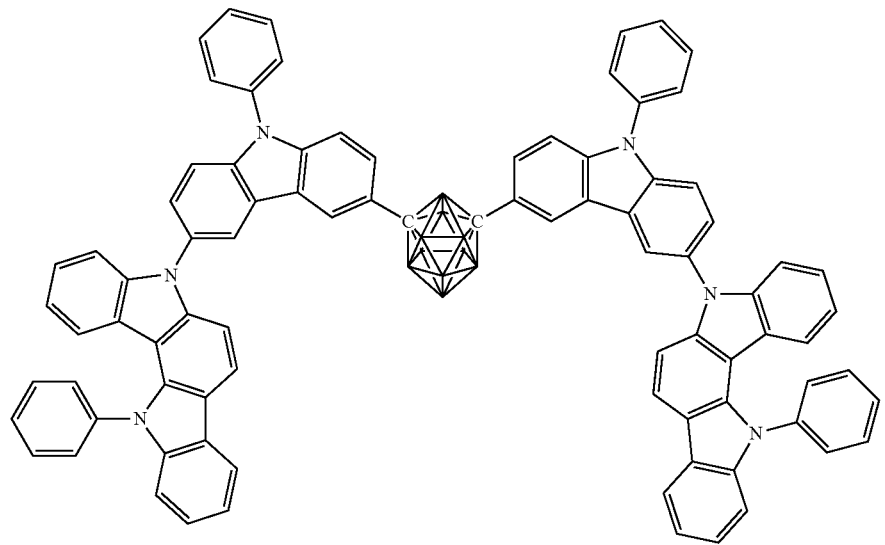
8
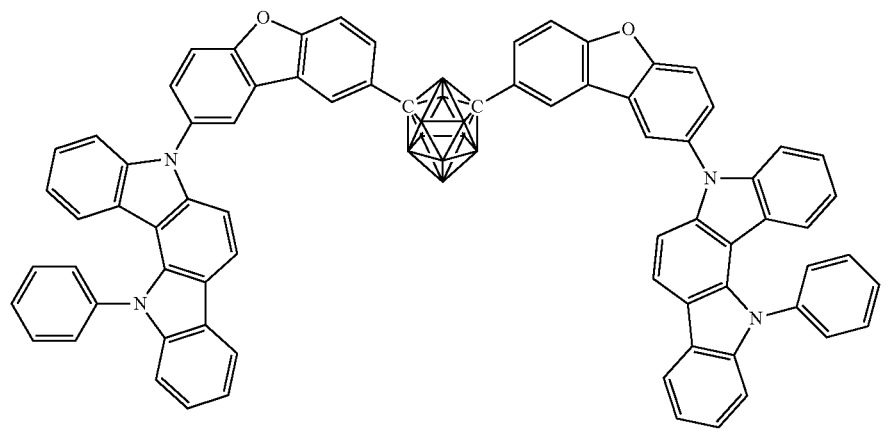
9
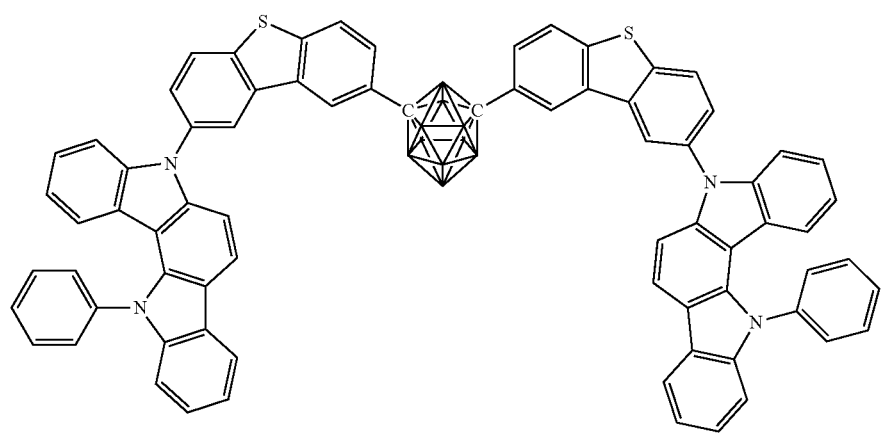

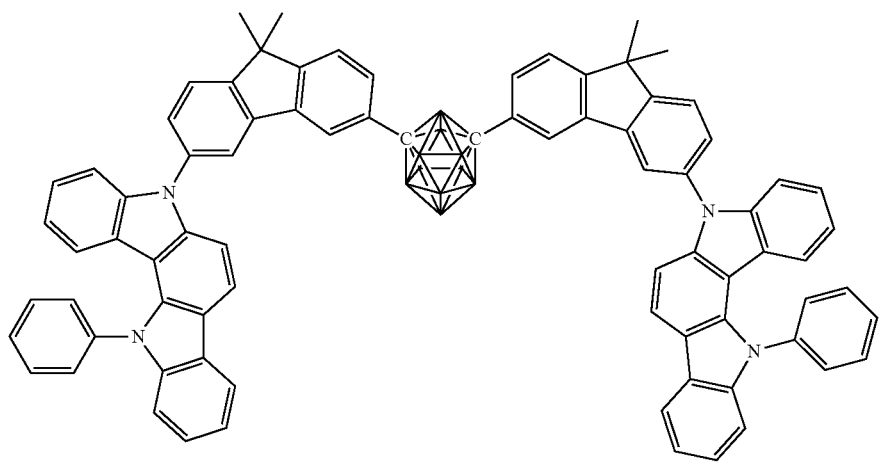
10
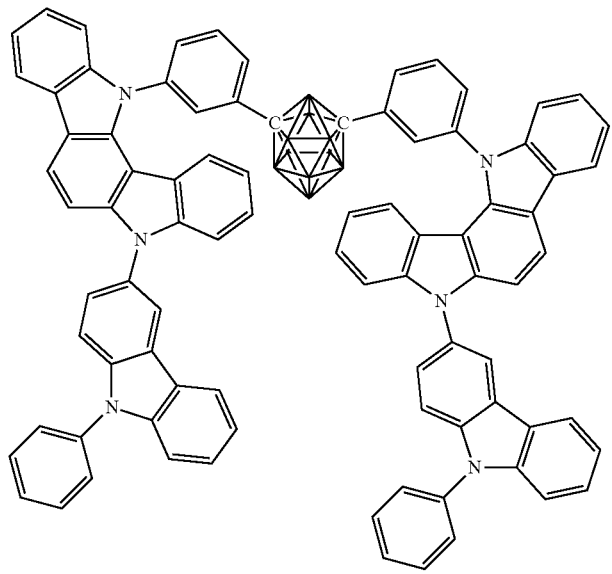
11
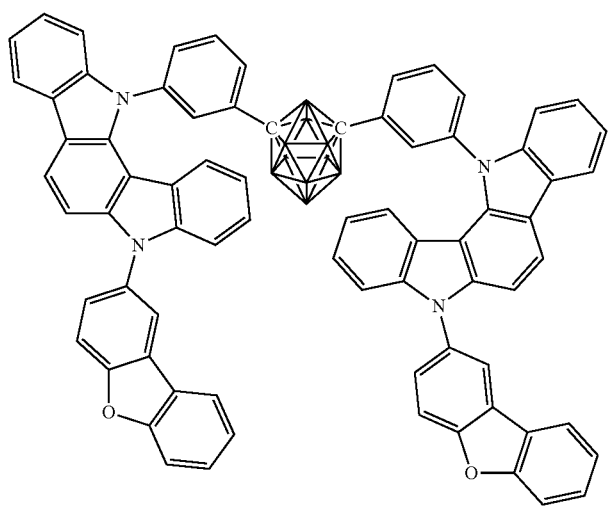
12

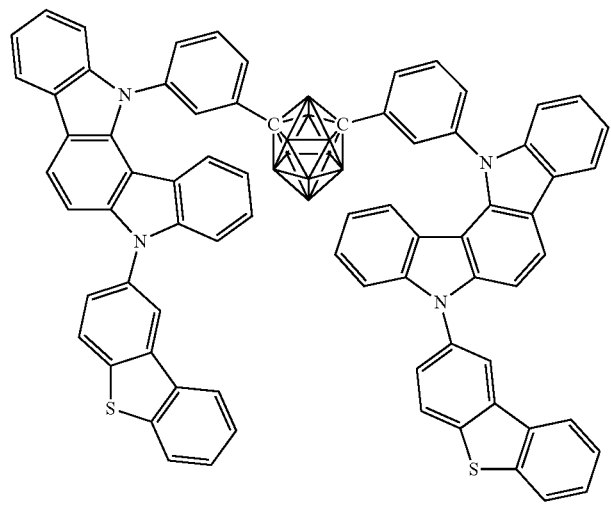
13
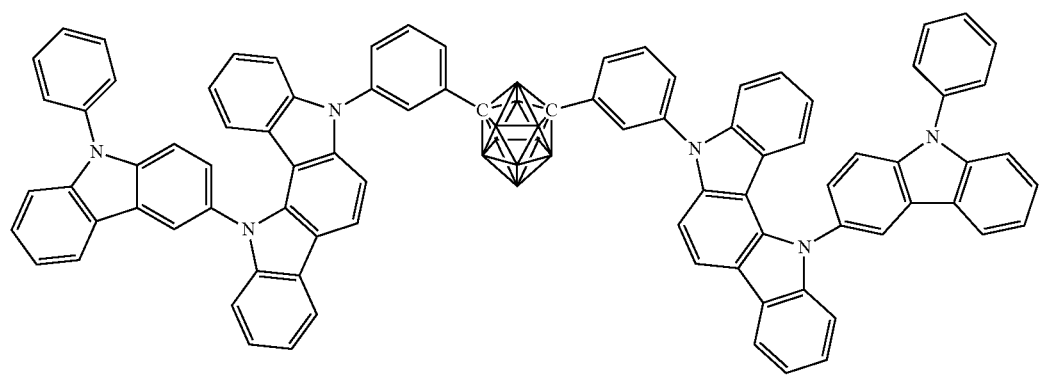
14
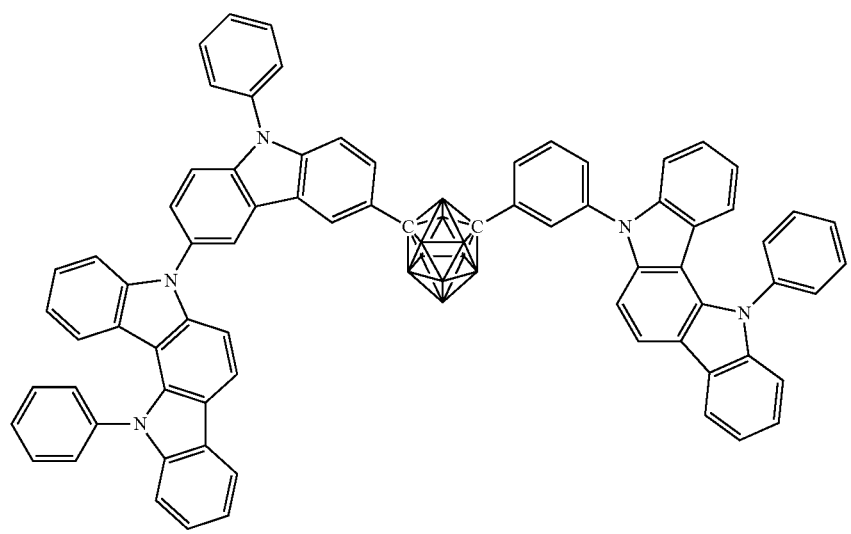
15

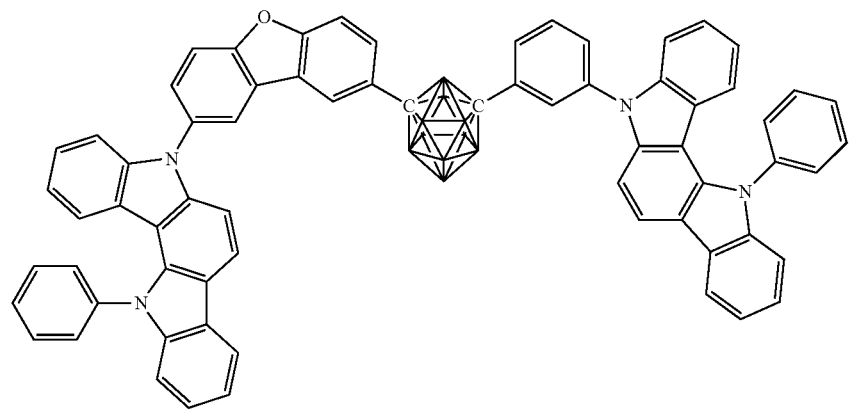
16
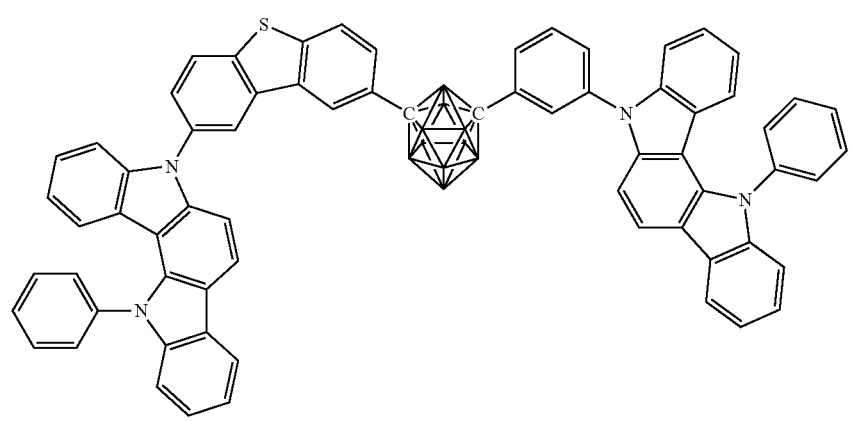
17
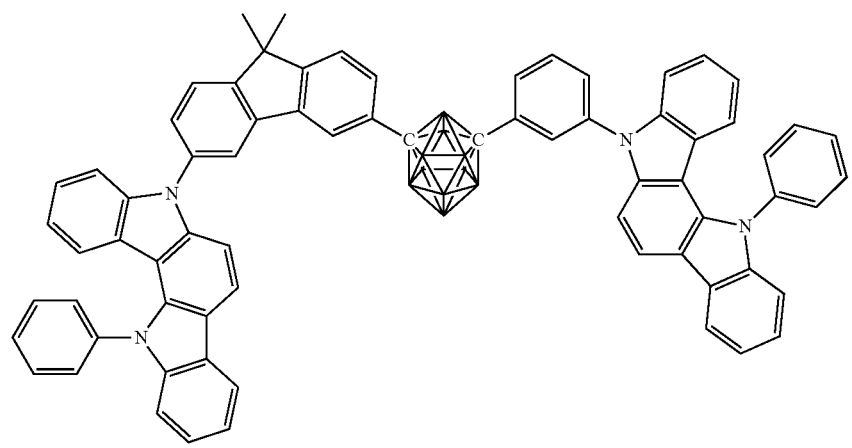
18

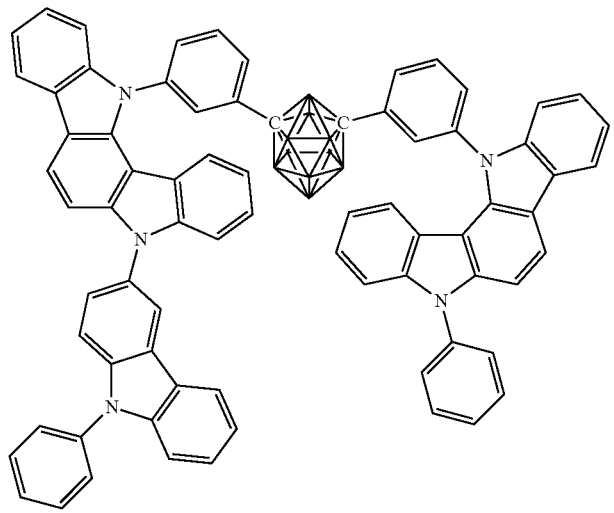
19
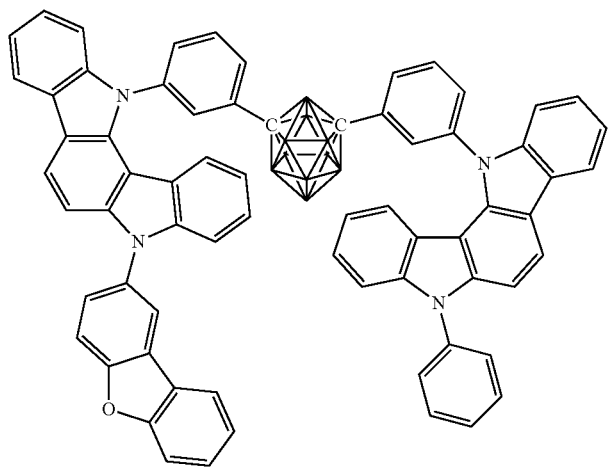
20
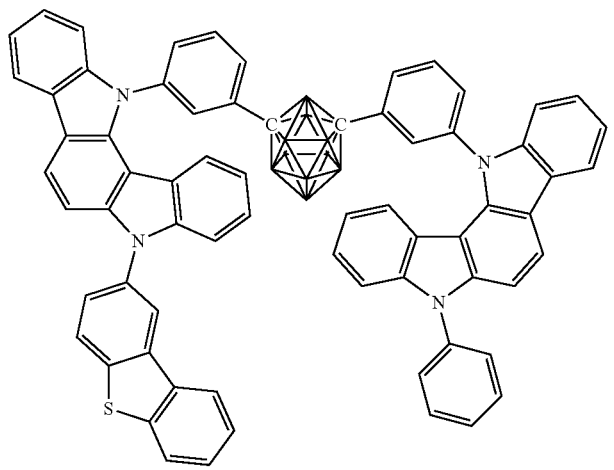
21

22
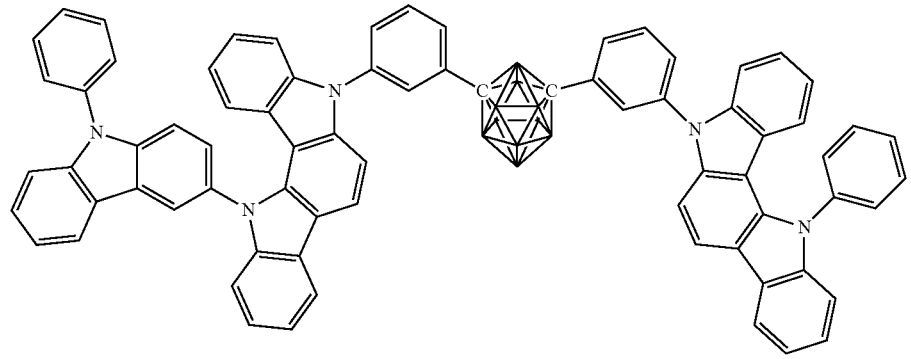
23
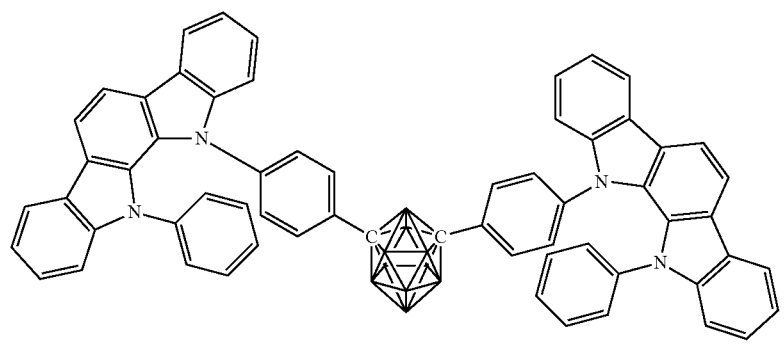
24
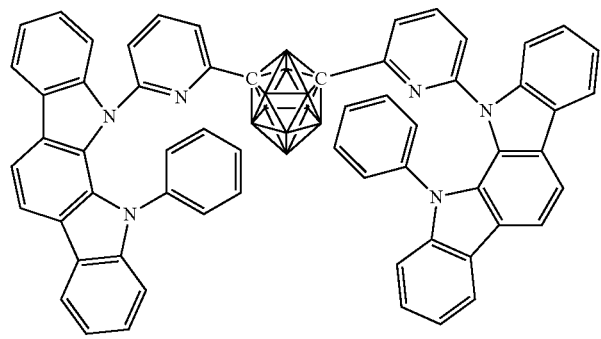
25
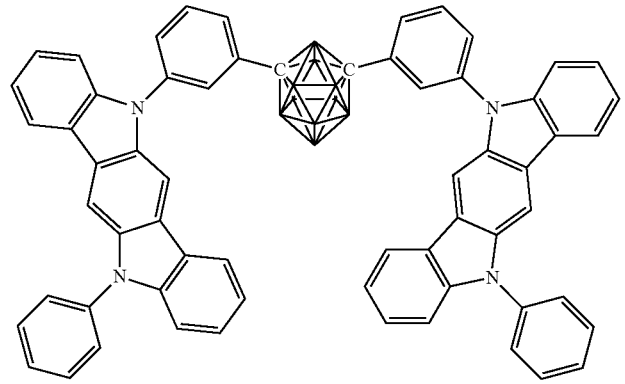

-continued
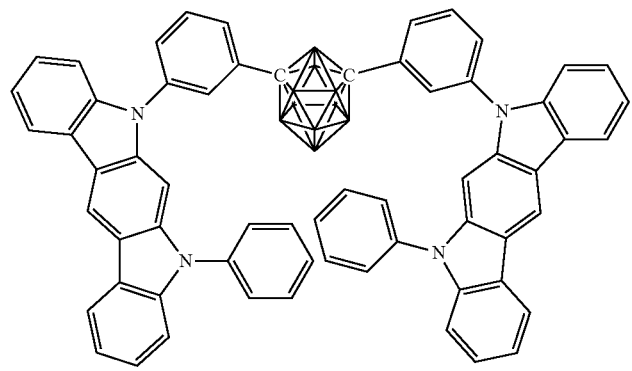
26
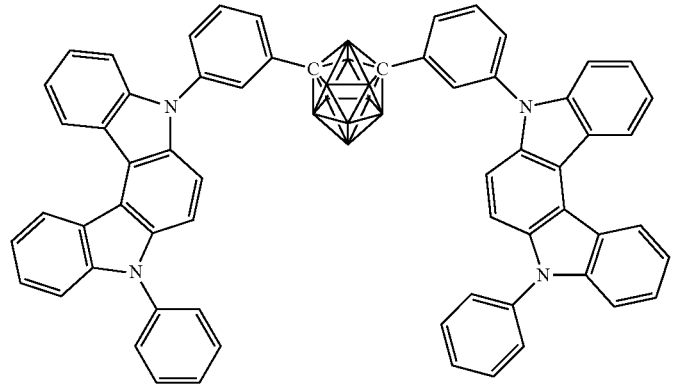
27
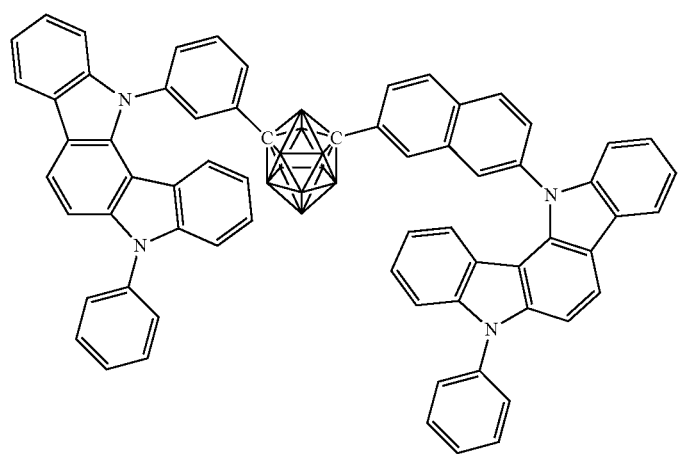
28
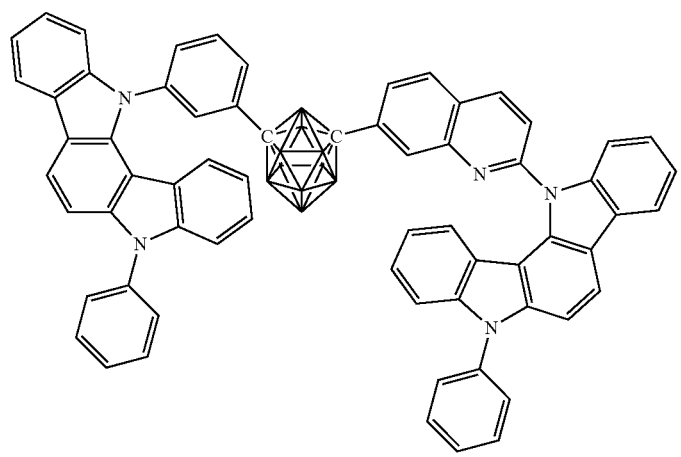
29

-continued
30
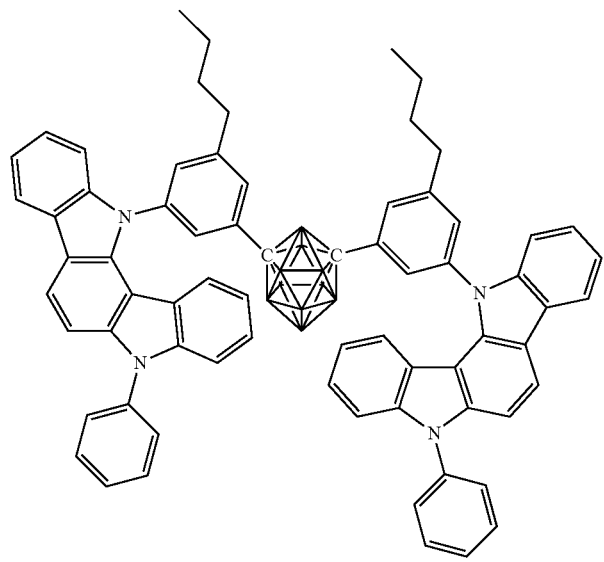
31
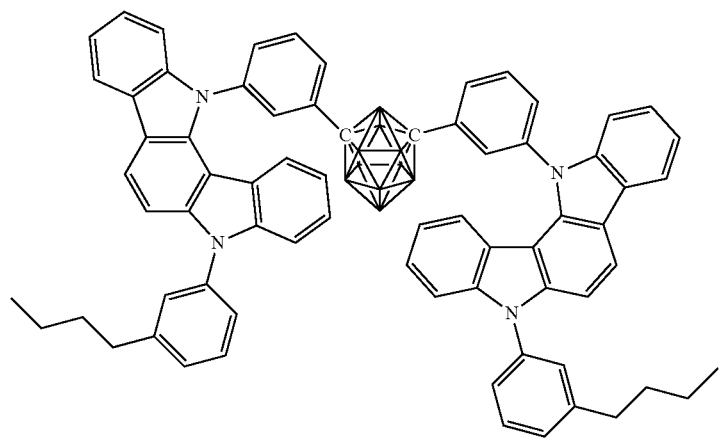
32
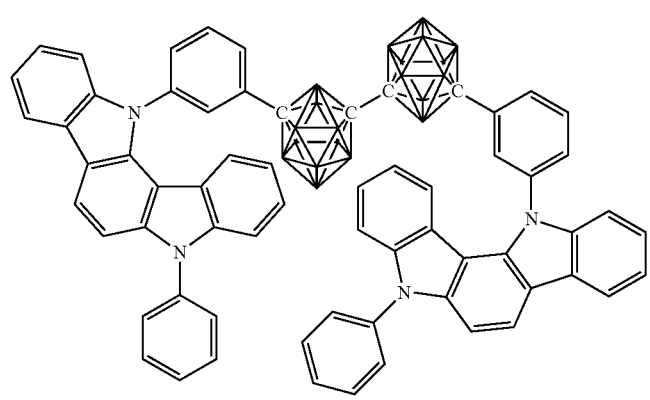

33
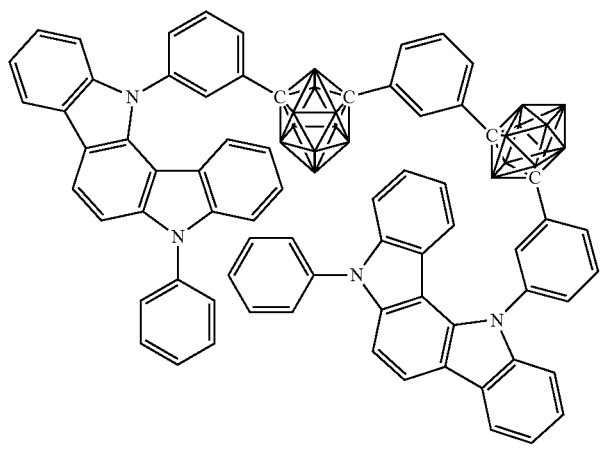
34
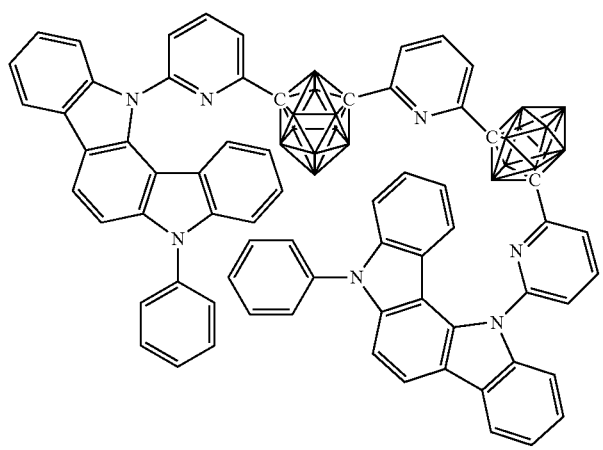
34-2
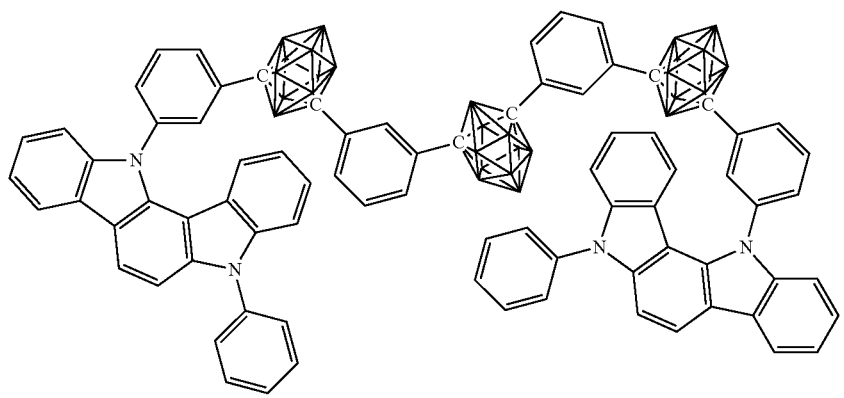
35
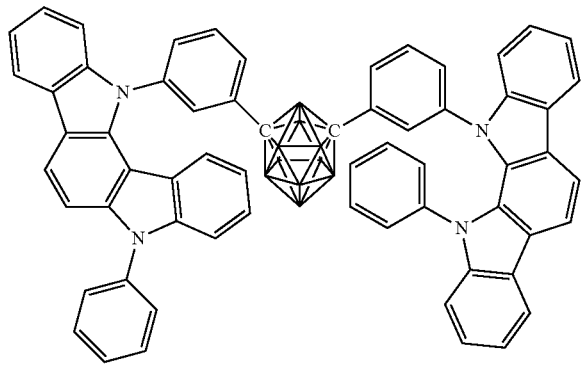

36
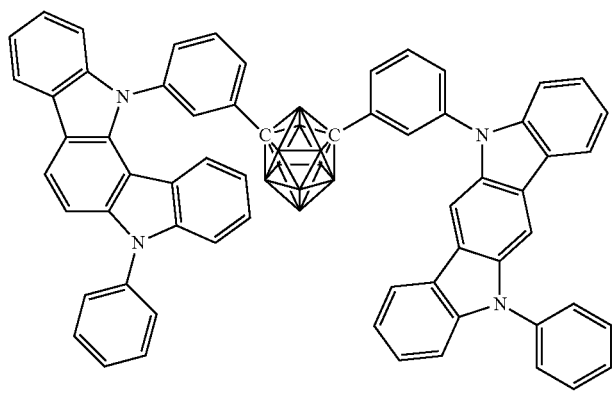
37
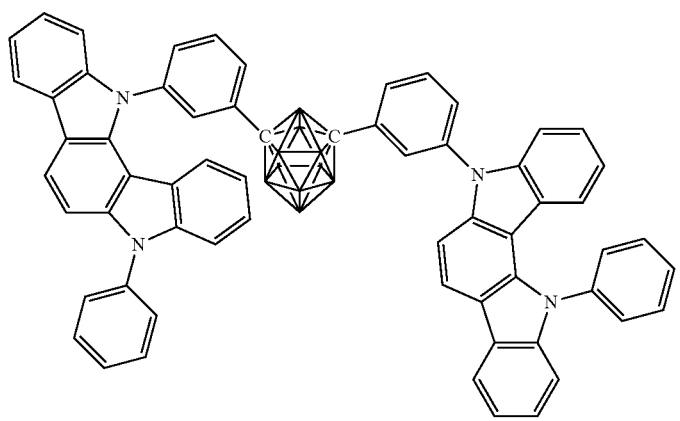
38
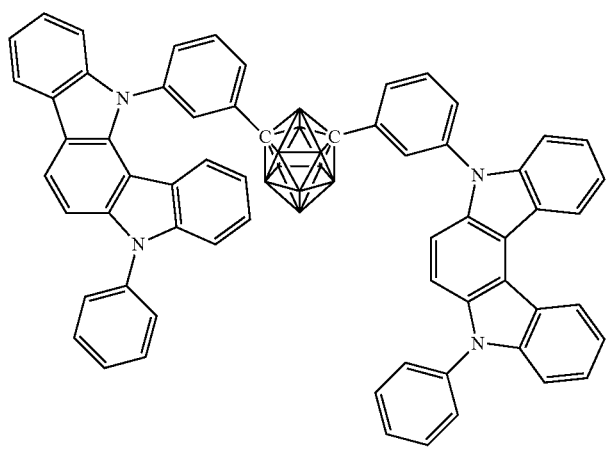
39
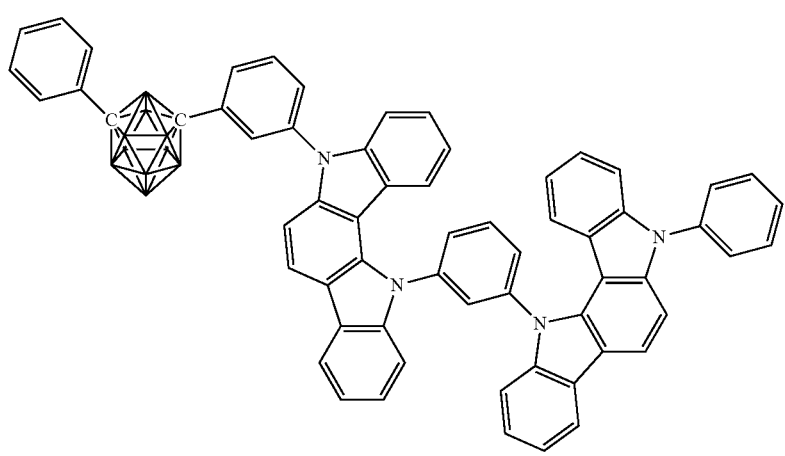

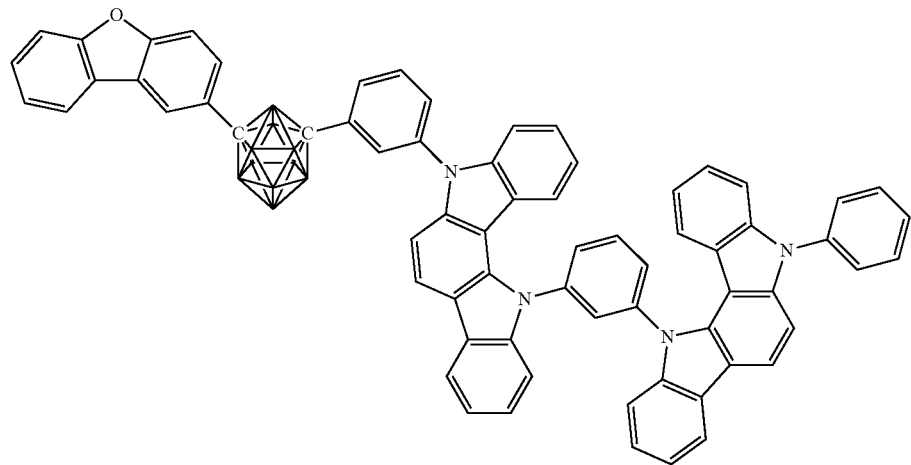
40
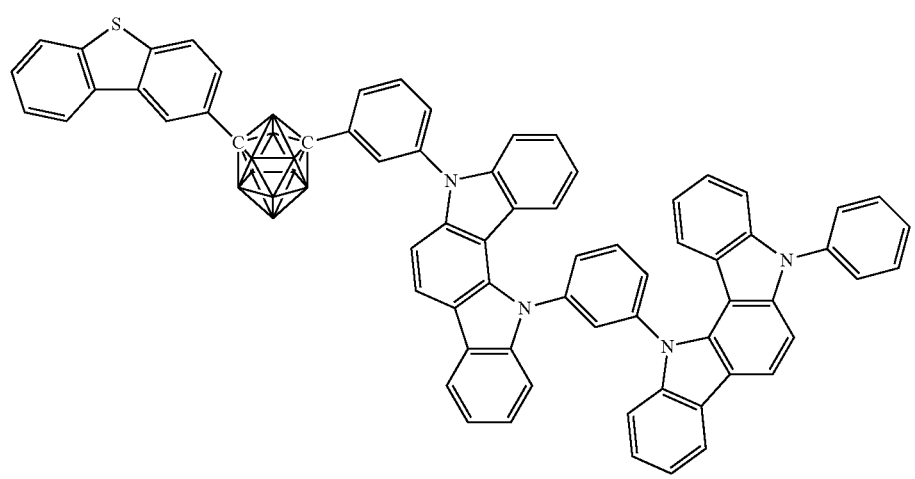
41
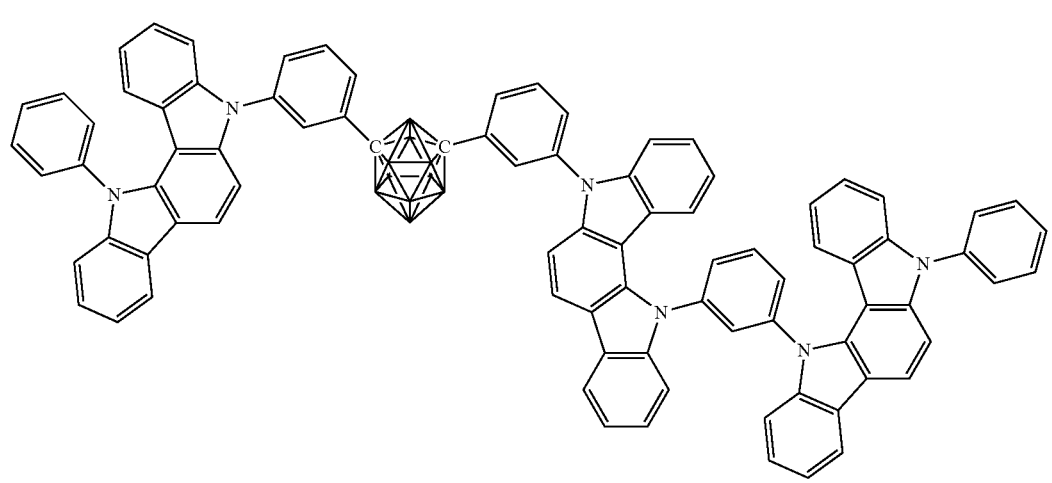
42

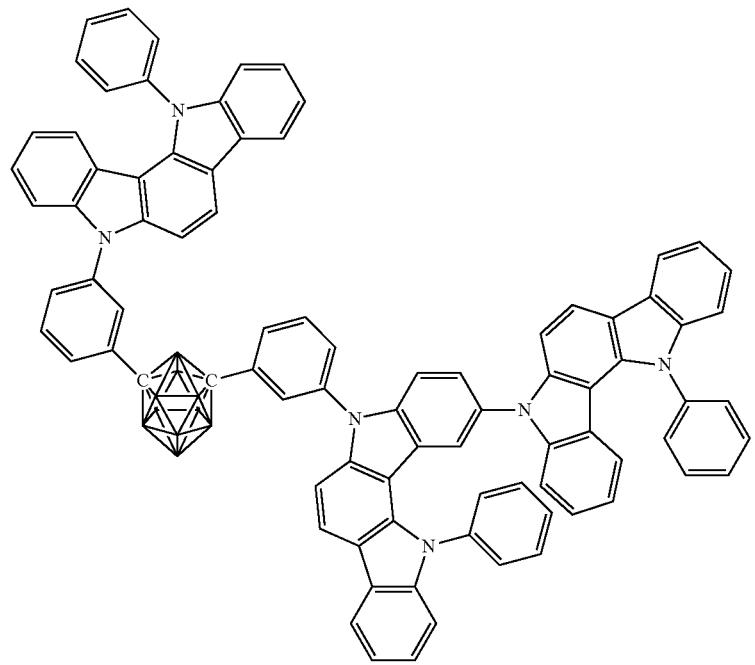
43
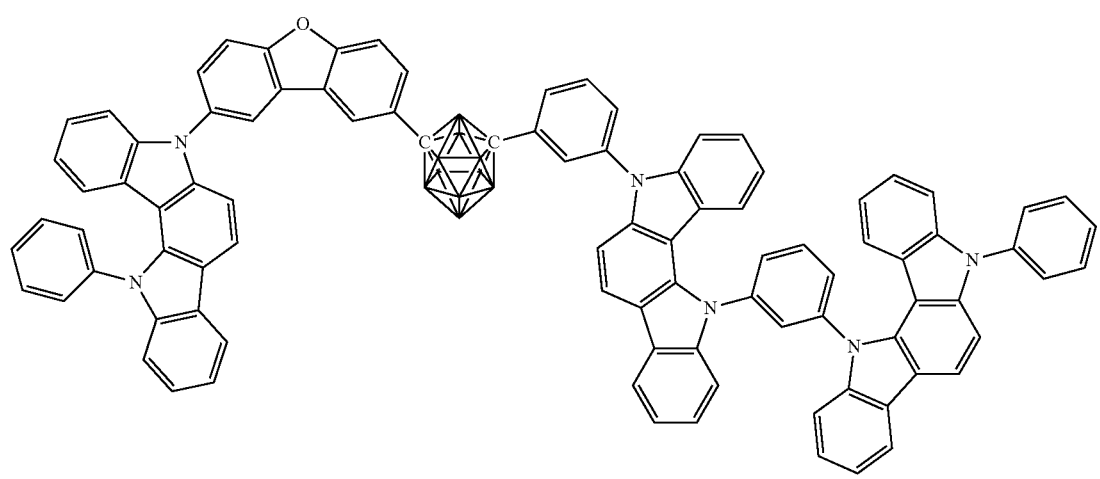
44
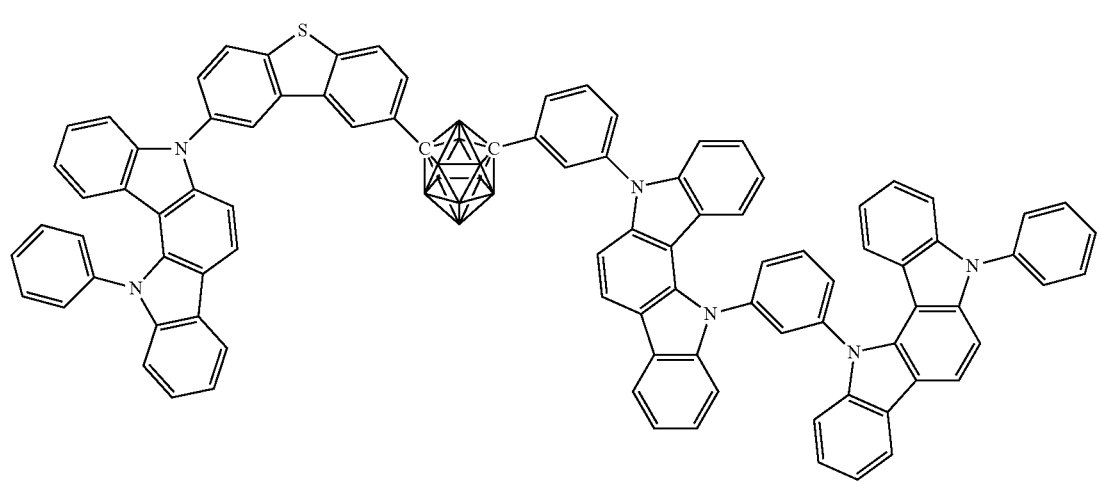
45

-continued

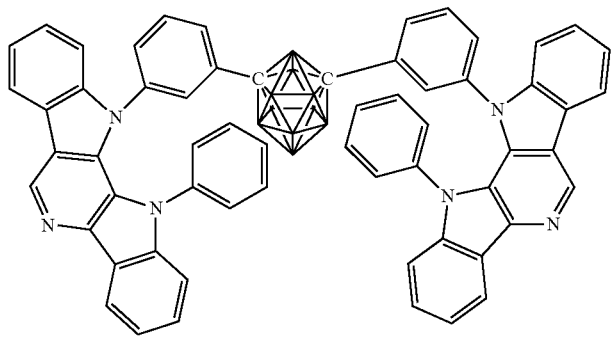

46

The material for an organic electroluminescent device of the present invention is formed of the carborane compound represented by the general formula (1). In view of the foregoing, the material for an organic electroluminescent device of the present invention is also referred to as, for example, "carborane compound of the present invention," "compound represented by the general formula (1)," or "material of the present invention."

When the material for an organic electroluminescent device of the present invention is contained in at least one of a plurality of organic layers of an organic EL device having a structure in which an anode, the plurality of organic layers, and a cathode are laminated on a substrate, an excellent organic electroluminescent device is provided. A light-emitting layer, an electron-transporting layer, or a hole-blocking layer is suitable as the organic layer in which the material is contained. Here, when the compound of the present invention is used in the light-emitting layer, the compound can be used as a host material for the light-emitting layer containing a fluorescent light-emitting, delayed fluorescent light-emitting, or phosphorescent light-emitting dopant. In addition, the compound of the present invention can be used as an organic light-emitting material that radiates fluorescence and delayed fluorescence. When the compound of the present invention is used as an organic light-emitting material that radiates fluorescence and delayed fluorescence, any other organic compound having a value for at least one of excited singlet energy or excited triplet energy higher than that of the compound is preferably used as the host material. The compound of the present invention is particularly preferably incorporated as a host material for the light-emitting layer containing the phosphorescent light-emitting dopant.

Next, an organic EL device using the material for an organic electroluminescent device of the present invention is described.

The organic EL device of the present invention includes organic layers including at least one light-emitting layer between an anode and a cathode laminated on a substrate. In addition, at least one of the organic layers contains the material for an organic electroluminescent device of the present invention. The material for an organic electroluminescent device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

The FIGURE is a sectional view for illustrating an example of the structure of a general organic EL device used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. The hole-injecting/transporting layer means any one or both of the hole-injecting layer and the hole-transporting layer, and the electron-injecting/transporting layer means any one or both of an electron-injecting layer and the electron-transporting layer.

It is possible to adopt a reverse structure as compared to the FIGURE, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials, such as CuI, indium tin oxide (ITO), $SnO_2$, and ZnO. In addition, a material such as IDIXO ($In_2O_3$—ZnO), which can produce an amorphous, transparent conductive film, may be used. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 µm or more), a pattern may be formed via a mask having a desired shape when any of the above-mentioned electrode substances is subjected to vapor deposition or sputtering. Alternatively, when a coatable substance, such as an organic conductive compound, is used, a wet film-forming method, such as a printing method or a coating method, may be used. When luminescence is taken out from the anode, the transmittance of the anode is desirably controlled to more than 10%. In addition, the sheet resistance of the anode is preferably several hundred ohms per square ($\Omega/\square$) or less. Further, the thickness of the film is, depending on its material, selected from the range of generally from 10 nm to 1,000 nm, preferably from 10 nm to 200 nm.

—Cathode—

Meanwhile, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal, which is a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum, is suitable from the viewpoints of an electron-injecting property and durability against oxidation or the like. The cathode can be produced by forming any of those electrode substances into a thin film by using a method such as vapor deposition or sputtering. In addition, the sheet resistance of the cathode is preferably several hundred $\Omega/\square$ or less, and the thickness of the film is selected from the range of generally from 10 nm to 5 µm, preferably from 50 nm to 200 nm. In order for luminescence produced to pass through, any one of the anode and cathode of the organic EL device is preferably transparent or semi-transparent, because the light emission luminance improves.

In addition, after the above-mentioned metal has been formed into a film having a thickness of from 1 nm to 20 nm as a cathode, the conductive transparent material mentioned in the description of the anode is formed into a film on the cathode, thereby being able to produce a transparent or semi-transparent cathode. Through the application of this, a device in which both the anode and cathode have transparency can be produced.

—Light-emitting Layer—

The light-emitting layer is a layer that emits light after the production of an exciton by the recombination of a hole injected from the anode and an electron injected from the cathode, and the light-emitting layer contains an organic light-emitting material and a host material.

When the light-emitting layer is a fluorescent light-emitting layer, at least one kind of fluorescent light-emitting material may be used alone as the fluorescent light-emitting material. However, it is preferred that the fluorescent light-emitting material be used as a fluorescent light-emitting dopant and the host material be contained.

The carborane compound represented by the general formula (1) can be used as the fluorescent light-emitting material in the light-emitting layer. However, the fluorescent light-emitting material is known through, for example, many patent literatures, and hence can be selected therefrom. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bis-styrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of an 8-quinolinol derivative, and a metal complex, rare earth complex, or transition metal complex of a pyrromethene derivative, polymer compounds, such as polythiophene, polyphenylene, and polyphenylene vinylene, and an organic silane derivative. Of those, for example, the following compound is preferred: a fused aromatic compound, a styryl compound, a diketopyrrolopyrrole compound, an oxazine compound, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, or benzothiophanthrene. Those compounds may each have an alkyl group, aryl group, aromatic heterocyclic group, or diarylamino group as a substituent.

The carborane compound represented by the general formula (1) can be used as a fluorescent host material in the light-emitting layer. However, the fluorescent host material is known through, for example, many patent literatures, and hence can be selected therefrom. For example, the following material can be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid compound typified by tris(8-quinolinato)aluminum (III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, or a polythiophene derivative. However, the fluorescent host material is not particularly limited thereto.

When the fluorescent light-emitting material is used as a fluorescent light-emitting dopant and the host material is contained, the content of the fluorescent light-emitting dopant in the light-emitting layer desirably falls within the range of from 0.01 wt % to 20 wt %, preferably from 0.1 wt % to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, it is said that 25% of the produced excitons are excited to a singlet excited state and the remaining 75% of the excitons are excited to a triplet excited state. As described in Advanced Materials 2009, 21, 4802-4806, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of thermal energy to radiate fluorescence, thereby expressing thermally activated delayed fluorescence. The organic EL device of the present invention can also express delayed fluorescence. In this case, the light emission can include both fluorescent light emission and delayed fluorescent light emission. Light emission from the host material may be present in part of the light emission.

When the light-emitting layer is a delayed fluorescent light-emitting layer, at least one kind of delayed fluorescent light-emitting material may be used alone as a delayed fluorescent light-emitting material. However, it is preferred that the delayed fluorescent light-emitting material be used as a delayed fluorescent light-emitting dopant and the host material be contained.

Although the carborane compound represented by the general formula (1) can be used as the delayed fluorescent light-emitting material in the light-emitting layer, a material selected from known delayed fluorescent light-emitting materials can also be used. Examples thereof include a tin complex, an indolocarbazole derivative, a copper complex, and a carbazole derivative. Specific examples thereof include, but not limited to, compounds described in the following non patent literatures and patent literature.

(1) Adv. Mater. 2009, 21, 4802-4806, (2) Appl. Phys. Lett. 98, 083302 (2011), (3) JP 2011-213643 A, and (4) J. Am. Chem. Soc. 2012, 134, 14706-14709.

Specific examples of the delayed fluorescent light-emitting material are shown below, but the delayed fluorescent light-emitting material is not limited to the following compounds.

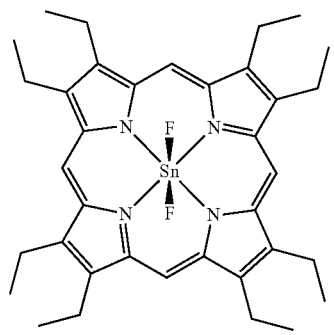

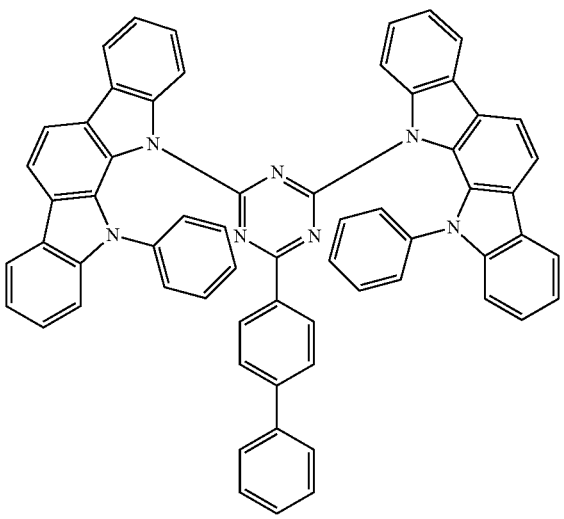

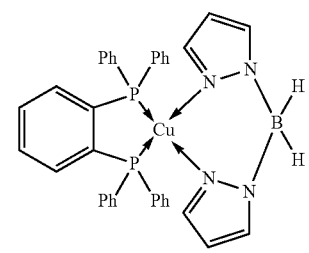

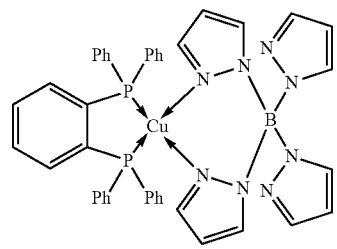

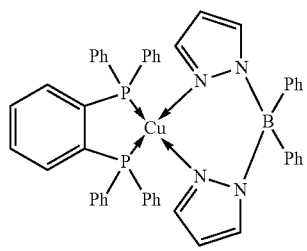

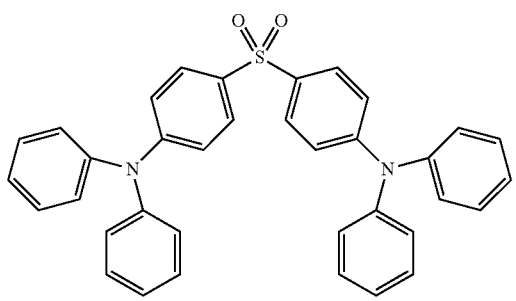

-continued

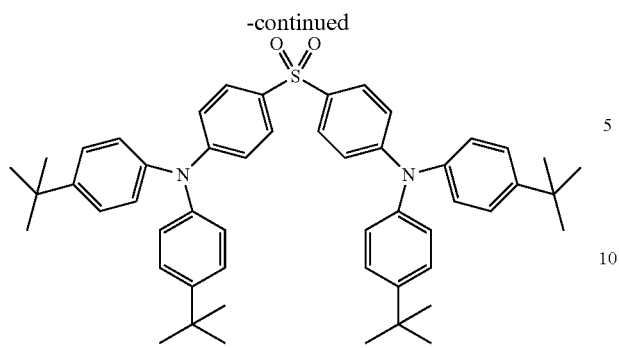

When the delayed fluorescent light-emitting material is used as a delayed fluorescent light-emitting dopant and the host material is contained, the content of the delayed fluorescent light-emitting dopant in the light-emitting layer desirably falls within the range of from 0.01 wt % to 50 wt %, preferably from 0.1 wt % to 20 wt %, more preferably from 0.01% to 10%.

The carborane compound represented by the general formula (1) can be used as the delayed fluorescent host material in the light-emitting layer. However, the delayed fluorescent host material can also be selected from compounds except the carborane. For example, the following compound can be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid compound typified by tris(8-quinolinato)aluminum (III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

When the light-emitting layer is a phosphorescent light-emitting layer, the light-emitting layer contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold.

Preferred examples of the phosphorescent light-emitting dopant include complexes such as Ir(ppy)$_3$, complexes such as Ir(bt)$_2$.acac$_3$, and complexes such as PtOEt$_3$, the complexes each having a noble metal element, such as Ir, as a central metal. Specific examples of those complexes are shown below, but the complexes are not limited to the following compounds.

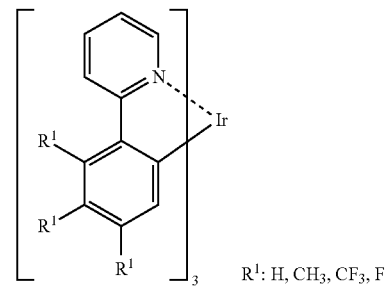

R$^1$: H, CH$_3$, CF$_3$, F

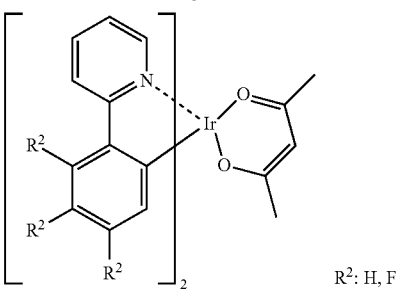

R$^2$: H, F

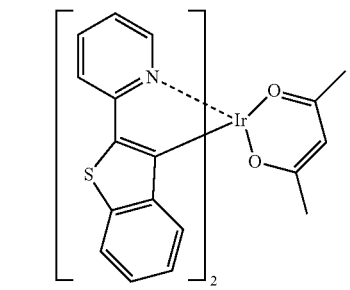

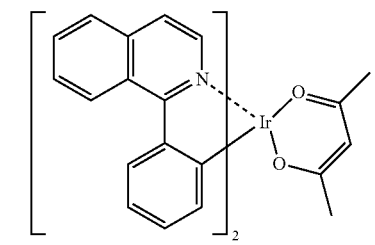

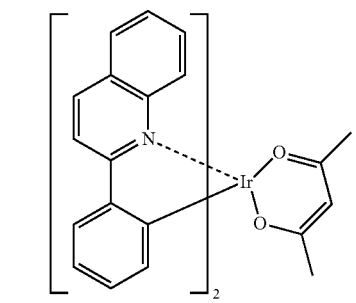

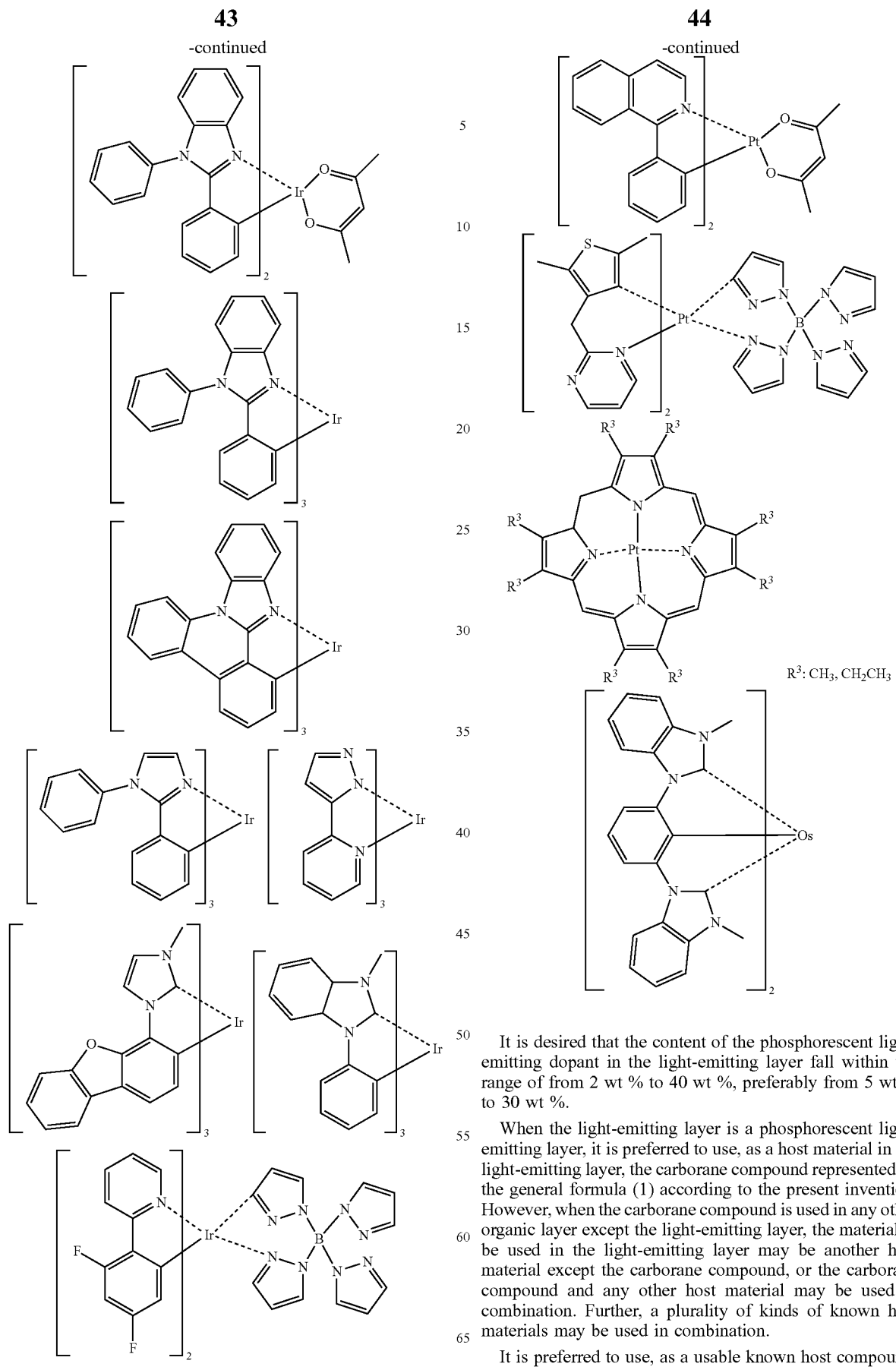

It is desired that the content of the phosphorescent light-emitting dopant in the light-emitting layer fall within the range of from 2 wt % to 40 wt %, preferably from 5 wt % to 30 wt %.

When the light-emitting layer is a phosphorescent light-emitting layer, it is preferred to use, as a host material in the light-emitting layer, the carborane compound represented by the general formula (1) according to the present invention. However, when the carborane compound is used in any other organic layer except the light-emitting layer, the material to be used in the light-emitting layer may be another host material except the carborane compound, or the carborane compound and any other host material may be used in combination. Further, a plurality of kinds of known host materials may be used in combination.

It is preferred to use, as a usable known host compound, a compound that has a hole-transporting ability or an electron-transporting ability, is capable of preventing luminescence from having a longer wavelength, and has a high glass transition temperature.

Any such other host material is known through, for example, many patent literatures, and hence can be selected therefrom. Specific examples of the host material include, but are not particularly limited to, an indole derivative, a carbazole derivative, an indolocarbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride, such as naphthalene perylene, a phthalocyanine derivative, various metal complexes typified by a metal complex of an 8-quinolinol derivative, a metal phthalocyanine, and metal complexes of benzoxazole and benzothiazole derivatives, and polymer compounds, such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

The light-emitting layer, which may be any one of a fluorescent light-emitting layer, a delayed fluorescent light-emitting layer, and a phosphorescent light-emitting layer, is preferably the phosphorescent light-emitting layer.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the carborane compound represented by the general formula (1) according to the present invention for the hole-blocking layer. However, when the carborane compound is used in any other organic layer, a known material for a hole-blocking layer may be used. In addition, a material for the electron-transporting layer to be described later can be used as a material for the hole-blocking layer as required.

—Electron-blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

A material for the hole-transporting layer to be described later can be used as a material for the electron-blocking layer as required. The thickness of the electron-blocking layer is preferably from 3 nm to 100 nm, more preferably from 5 nm to 30 nm.

—Exciton-blocking Layer—

The exciton-blocking layer refers to a layer for blocking excitons produced by the recombination of a hole and an electron in the light-emitting layer from diffusing into charge-transporting layers. The insertion of this layer enables efficient confinement of the excitons in the light-emitting layer, thereby being able to improve the luminous efficiency of the device. The exciton-blocking layer may be inserted on any of the anode side and the cathode side of the adjacent light-emitting layer, and may also be inserted simultaneously on both sides.

Although the carborane compound represented by the general formula (1) can be used as a material for the exciton-blocking layer, as other materials therefor, there are given, for example, 1,3-dicarbazolylbenzene (mCP) and bis (2-methyl-8-quinolinolato)-4-phenylphenolatoaluminum (III) (BAlq).

—Hole-transporting Layer—

The hole-transporting layer is formed of a hole-transporting material having a function of transporting holes, and a single hole-transporting layer or a plurality of hole-transporting layers can be formed.

The hole-transporting material has a hole-injecting property or a hole-transporting property or has an electron-blocking property, and any of an organic material and an inorganic material can be used as the hole-transporting material. Although it is preferred to use the carborane compound represented by the general formula (1) as a known hole-transporting material that can be used, any compound selected from conventionally known compounds can be used. Examples of the known hole-transporting material that can be used include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular weight oligomer, in particular, a thiophene oligomer. However, an aromatic tertiary amine compound, such as a phenylenediamine derivative or an arylamine derivative, is preferably used.

—Electron-transporting Layer—

The electron-transporting layer is formed of a material having a function of transporting electrons, and a single electron-transporting layer or a plurality of electron-transporting layers can be formed.

An electron-transporting material (which also serves as a hole-blocking material in some cases) only needs to have a function of transferring electrons injected from the cathode into the light-emitting layer. Although it is preferred to use the carborane compound represented by the general formula (1) according to the present invention for the electron-transporting layer, any compound selected from conventionally known compounds can be used. Examples thereof include a nitro-substituted fluorene derivative, a diphenylquinone derivative, a thiopyran dioxide derivative, a carbodiimide, a fluorenylidenemethane derivative, anthraquinodimethane and anthrone derivatives, and an oxadiazole derivative. Further, a thiadiazole derivative prepared by substituting an oxygen atom on an oxadiazole ring with a sulfur atom in the oxadiazole derivative or a quinoxaline derivative that has a quinoxaline ring known as an electron

47 withdrawing group can be used as the electron-transporting material. Further, a polymer material in which any such material is introduced in a polymer chain or is used as a polymer main chain can be used.

EXAMPLES

Now, the present invention is described in more detail by way of Examples. It should be appreciated that the present invention is not limited to Examples below and can be carried out in various forms as long as the various forms do not deviate from the gist of the present invention.

The route described below was used to synthesize a carborane compound to be used as a material for an organic electroluminescent device. The number of each compound corresponds to the number given to the chemical formula.

Example 1

A compound 3 is synthesized in accordance with the following reaction formulae.

48

Under a nitrogen atmosphere, 21.2 g (0.147 mol) of m-carborane and 210 mL of 1,2-dimethoxyethane (DME) were added, and the resultant DME solution was cooled to 0° C. 118.7 mL of a 2.65 M solution of n-butyllithium in hexane was dropped to the solution, and the mixture was stirred under ice cooling for 30 min. 80 mL of pyridine was added to the resultant and the mixture was stirred at room temperature for 30 min. After that, 90.2 g (0.911 mol) of copper (I) chloride was added to the resultant and the mixture was stirred at 65° C. for 30 min. After that, 100 g (0.353 mol) of p-bromoiodobenzene was added to the resultant and the mixture was stirred at 95° C. overnight. The reaction solution was cooled to room temperature, and then the precipitated crystal was taken by filtration and the solvent was distilled off under reduced pressure. The resultant residue was purified by silica gel column chromatography to provide 38.0 g (83.7 mmol, yield: 56.9%) of an intermediate A.

Under a nitrogen atmosphere, 38.0 g (83.7 mmol) of the intermediate A, 51.5 g (0.20 mol) of indolo[3,2-a]carbazole,

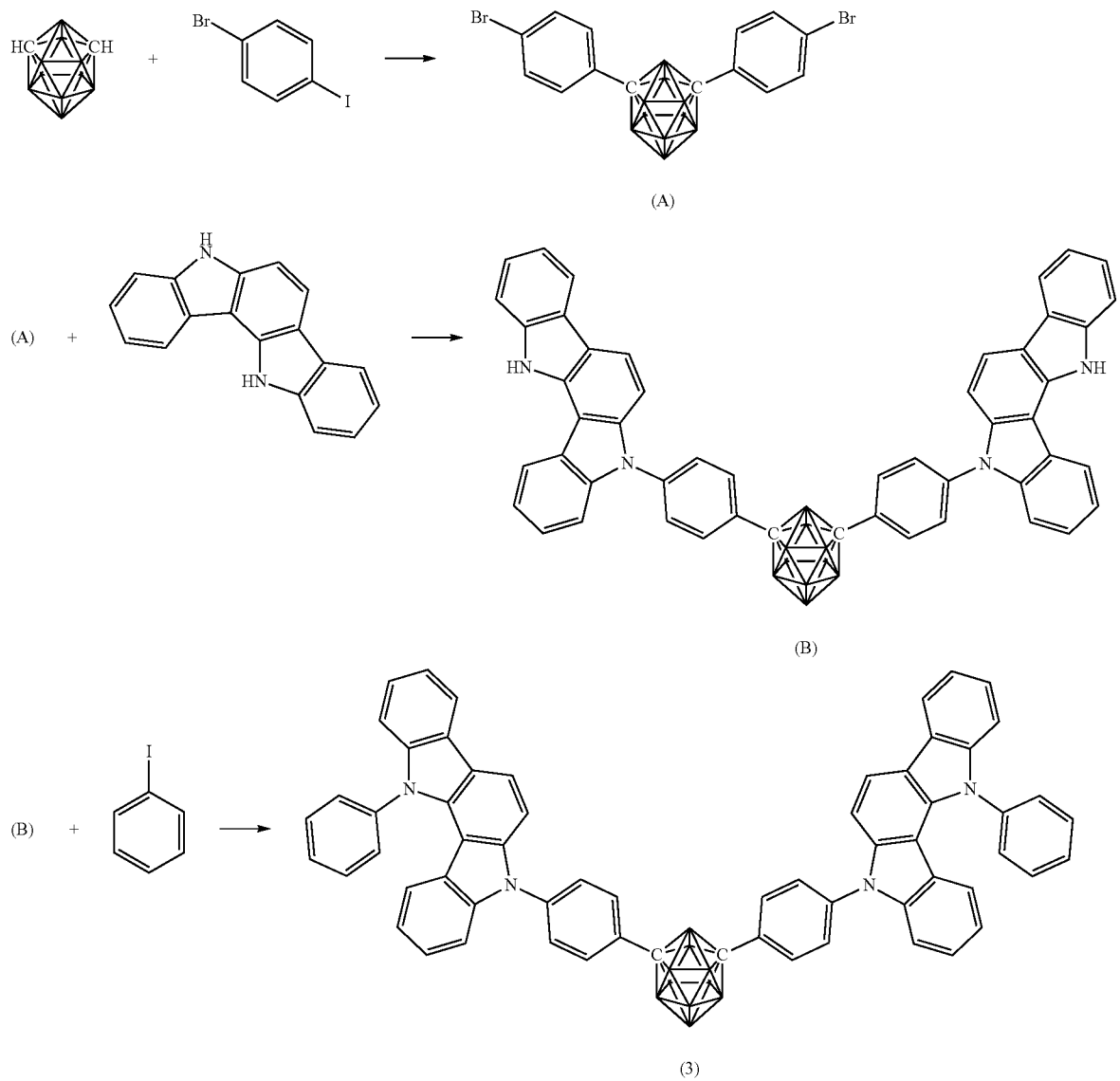

3.19 g (16.7 mmol) of copper iodide, 106 g (0.50 mol) of tripotassium phosphate, 19.1 g (0.17 mol) of trans-1,2-cyclohexanediamine, and 540 mL of 1,4-dioxane were added, and the mixture was stirred at 120° C. overnight. The reaction solution was cooled to room temperature, and then the precipitated crystal was taken by filtration and the solvent was distilled off under reduced pressure. The resultant residue was purified by silica gel column chromatography to provide 41.8 g (51.9 mmol, yield: 62.0%) of an intermediate B as a white solid.

Under a nitrogen atmosphere, 20.0 g (24.8 mmol) of the intermediate B, 607 g (2.96 mol) of iodobenzene, 20.5 g (0.32 mmol) of copper powder, and 75.4 g (0.55 mol) of potassium carbonate were added, and the mixture was stirred at 120° C. overnight. The reaction solution was cooled to room temperature, and then the precipitated crystal was taken by filtration and the solvent was distilled off under reduced pressure. The resultant residue was purified by silica gel column chromatography to provide 7.4 g (7.73 mmol, yield: 31.2%) of a compound 3. (APCI-TOFMS, m/z 958 [M+H]$^+$)

Compounds 4, 23, and 24, and the following compounds H-1 and H-2 were synthesized in conformity with the synthesis example and the synthesis method described herein.

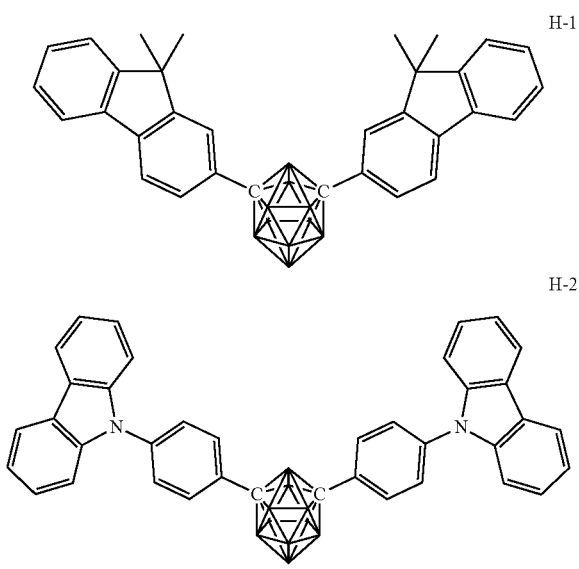

Example 2

Each thin film was laminated by a vacuum deposition method at a degree of vacuum of $2.0 \times 10^{-5}$ Pa on a glass substrate on which an anode formed of indium tin oxide (ITO) having a thickness of 70 mn had been formed. First, copper phthalocyanine (CuPC) was formed into a layer having a thickness of 30 nm to serve as a hole-injecting layer on the ITO. Next, diphenyl naphthyl diamine (NPD) was formed into a layer having a thickness of 15 nm to serve as a hole-transporting layer. Next, the compound 3 serving as a host material for a light-emitting layer and an iridium complex [iridium(III) bis(4,6-di-fluorophenyl)-pyridinato-N, C2']picolinate] (FIrpic) serving as a blue phosphorescent material as a dopant were co-deposited from different deposition sources onto the hole-transporting layer to form a light-emitting layer having a thickness of 30 nm. The concentration of FIrpic was 20%. Next, Alq$_3$ was formed into a layer having a thickness of 25 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. The resultant organic EL device has such a layer construction that the electron-injecting layer is added between the cathode and the electron-transporting layer in the organic EL device illustrated in the FIGURE.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values at 2.5 mA/cm$^2$ (initial characteristics). The maximum wavelength of the emission spectrum of the device was 475 nm, and hence the acquisition of light emission from FIrpic was found.

Examples 3 to 5

Organic EL devices were each produced in the same manner as in Example 2 except that the compound 4, 23, or 24 was used instead of the compound 3 as the host material for the light-emitting layer in Example 2.

Comparative Example 1

An organic EL device was produced in the same manner as in Example 2 except that mCP was used instead of the compound 3 as the host material for the light-emitting layer in Example 2.

Comparative Examples 2 and 3

Organic EL devices were each produced in the same manner as in Example 2 except that the compound H-1 or H-2 was used instead of the compound 3 as the host material for the light-emitting layer in Example 2.

The organic EL devices obtained in Examples 3 to 5 and Comparative Examples 1 to 3 were evaluated in the same manner as in Example 2. As a result, it was confirmed that the devices had such light-emitting characteristics as shown in Table 1. The maximum wavelength of each of the emission spectra of the organic EL devices obtained in Examples 3 to 5 and Comparative Examples 1 to 3 was 475 nm, and hence the acquisition of light emission from FIrpic was identified.

TABLE 1

| | Host material compound | Luminance (cd/m$^2$) | Voltage (V) | Visual luminous efficiency (lm/W) |
|---|---|---|---|---|
| Example 2 | 3 | 220 | 7.3 | 3.8 |
| Example 3 | 4 | 220 | 7.1 | 3.9 |
| Example 4 | 23 | 190 | 7.6 | 3.2 |
| Example 5 | 24 | 190 | 7.1 | 3.4 |
| Comparative Example 1 | mCP | 140 | 8.7 | 2.0 |
| Comparative Example 2 | H-1 | 100 | 7.7 | 1.6 |
| Comparative Example 3 | H-2 | 140 | 7.5 | 2.3 |

Example 6

Each thin film was laminated by a vacuum deposition method at a degree of vacuum of 2.0×10⁻⁵ Pa on a glass substrate on which an anode formed of indium tin oxide (ITO) having a thickness of 70 nm had been formed. First, copper phthalocyanine (CuPC) was formed into a layer having a thickness of 30 nm to serve as a hole-injecting layer on the ITO. Next, diphenyl naphthyl diamine (NPD) was formed into a layer having a thickness of 15 nm to serve as a hole-transporting layer. Next, the compound 3 serving as a host material for a light-emitting layer and Ir(ppy)$_3$ serving as a dopant were co-deposited from different deposition sources onto the hole-transporting layer to form a light-emitting layer having a thickness of 30 nm. The concentration of Ir(ppy)$_3$ was 10%. Next, Alq$_3$ was formed into a layer having a thickness of 25 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 2. The columns "luminance", "voltage", and "luminous efficiency" in Table 2 show values at the time of driving at 20 mA/cm² (initial characteristics). The maximum wavelength of the emission spectrum of the device was 530 nm, and hence the acquisition of light emission from Ir(ppy)$_3$ was found.

Examples 7 to 9

Organic EL devices were each produced in the same manner as in Example 6 except that the compound 4, 23, or 24 was used instead of the compound 3 as the host material for the light-emitting layer in Example 6.

Comparative Examples 4 to 6

Organic EL devices were each produced in the same manner as in Example 6 except that CBP, H-1, or H-2 was used instead of the compound 3 as the host material for the light-emitting layer in Example 6.

The organic EL devices obtained in Examples 7 to 9 and Comparative Examples 4 to 6 were evaluated in the same manner as in Example 6. As a result, it was confirmed that the devices had such light-emitting characteristics as shown in Table 2. The maximum wavelength of each of the emission spectra of the organic EL devices obtained in Examples 7 to 9 and Comparative Examples 4 to 6 was 530 nm, and hence the acquisition of light emission from Ir(ppy)$_3$ was identified.

TABLE 2

| | Host material compound | Luminance (cd/m²) | Voltage (V) | Visual luminous efficiency (lm/W) |
|---|---|---|---|---|
| Example 6 | 3 | 2,100 | 8.8 | 3.7 |
| Example 7 | 4 | 2,100 | 8.5 | 3.9 |
| Example 8 | 23 | 2,000 | 9.1 | 3.4 |
| Example 9 | 24 | 1,800 | 8.6 | 3.3 |
| Comparative Example 4 | CBP | 1,120 | 8.7 | 2.0 |
| Comparative Example 5 | H-1 | 1,200 | 8.5 | 2.2 |
| Comparative Example 6 | H-2 | 1,000 | 8.3 | 1.9 |

REFERENCE SIGNS LIST

1 substrate, 2 anode, 3 hole-injecting layer, 4 hole-transporting layer, 5 light-emitting layer, 6 electron-transporting layer, 7 cathode

The invention claimed is:

1. An organic electroluminescent device having a structure in which an anode, organic layers, and a cathode are laminated on a substrate, wherein at least one layer of the organic layers comprises an organic layer containing a material for an organic electroluminescent device, the material for an organic electroluminescent device comprising a carborane compound represented by the general formula (1):

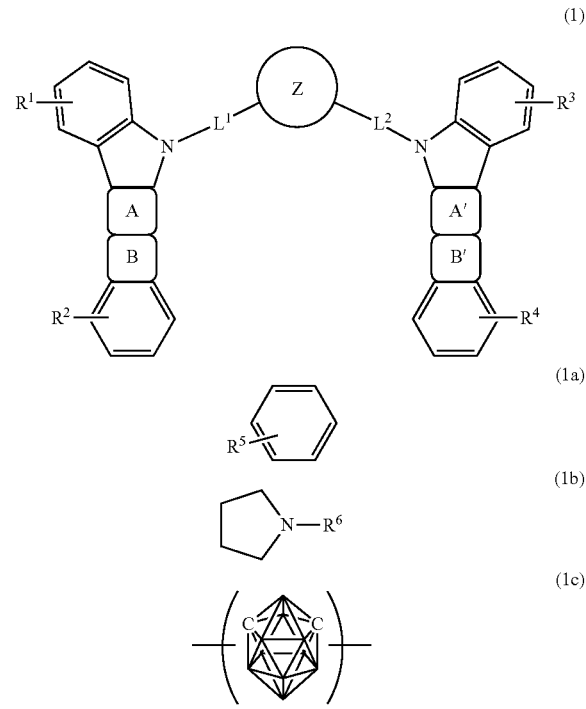

where:

a ring A and a ring A' each represent an aromatic ring represented by the formula (1a), the ring being fused with an adjacent ring at an arbitrary position, a ring B and a ring B' each represent a heterocycle represented by the formula (1b) whose nitrogen-containing five-membered ring is fused with an adjacent ring at an arbitrary position, and a ring Z represents a divalent carborane group $C_2B_{10}H_{10}$ represented by the formula (1c);

the formulae (1a) or the formulae (1b) present in the same molecule may be identical to or different from each other;

$L^1$ and $L^2$ each independently represent a phenyl group or a 6-membered nitrogen-containing aromatic heterocyclic group; and $R^1$, $R^2$, $R^3$, $R^4$, and $R^5$ each independently represent a hydrogen atom, and $R^6$ represents a phenyl group, wherein the organic layer containing the material for an organic electroluminescent device comprises a light-emitting layer containing a phosphorescent light-emitting dopant.

2. The organic electroluminescent device according to claim 1, wherein the material for an organic electroluminescent device is selected from the group consisting of:

3

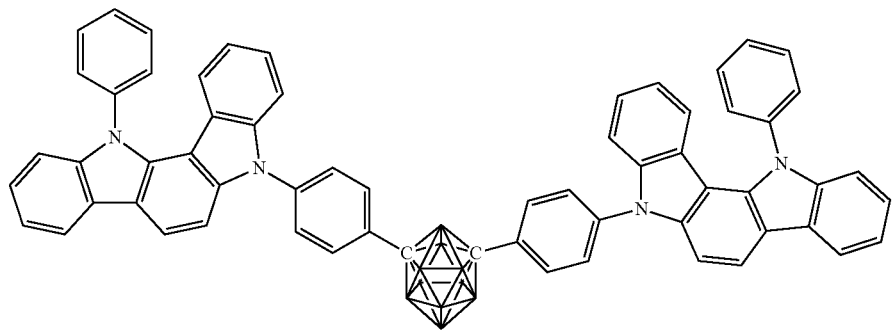

4

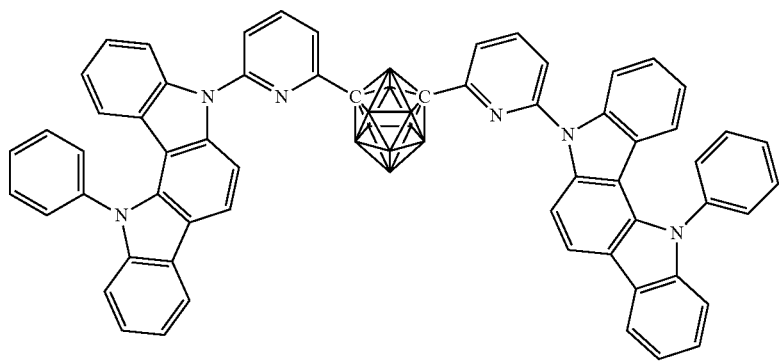

23

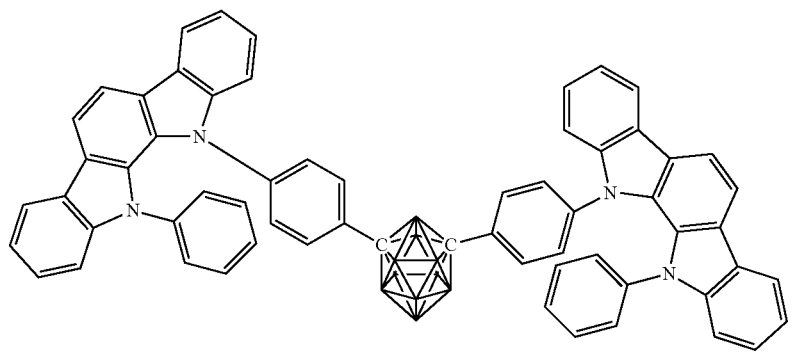

24

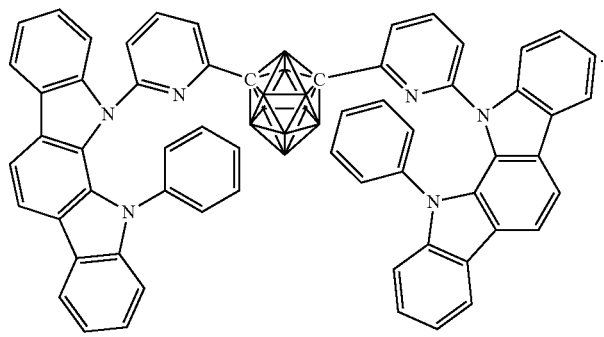

* * * * *